United States Patent [19]
Siegel et al.

[11] Patent Number: 5,100,890
[45] Date of Patent: Mar. 31, 1992

[54] ARYLMETHYLAZOLES AND THEIR SALTS, AGENTS WHICH CONTAIN THESE COMPOUNDS, AND THEIR USE

[75] Inventors: Herbert Siegel, Hofheim am Taunus; Klaus-Dieter Kampe, Bad Soden am Taunus; Hans-Georg Alpermann, Königstein; Hermann J. Gerhards, Hofheim am Taunus; Patricia Usinger, Eppstein; Ulrich Schacht, Hofheim am Taunus; Margret Leven, Kelkheim; Wolfgang Raether, Dreieich; Walter Dittmar, Hofheim am Taunus; Burkhard Sachse, Kelkheim, all of Fed. Rep. of Germany

[73] Assignee: Hoechst Aktiengesellschaft, Frankfurt am Main, Fed. Rep. of Germany

[21] Appl. No.: 411,256
[22] Filed: Sep. 25, 1989

Related U.S. Application Data

[63] Continuation of Ser. No. 909,598, Sep. 22, 1986, abandoned.

[30] Foreign Application Priority Data

Sep. 23, 1985 [DE] Fed. Rep. of Germany ....... 3533824
Nov. 23, 1985 [DE] Fed. Rep. of Germany ....... 3541429
Aug. 14, 1986 [DE] Fed. Rep. of Germany ....... 3627656
Aug. 22, 1986 [DE] Fed. Rep. of Germany ....... 3628545

[51] Int. Cl.$^5$ .................. A61K 31/535; C07D 233/54; C07D 401/00; C07D 413/00
[52] U.S. Cl. .................. 514/232.2; 548/341; 548/336; 546/210; 546/187; 514/397; 514/399; 514/235.8; 514/326; 514/316; 544/82; 544/139
[58] Field of Search ............... 548/341, 336; 544/132, 544/82, 139; 546/210, 187; 514/397, 399, 235.8, 326, 316, 232.2

[56] References Cited

U.S. PATENT DOCUMENTS

| | | | |
|---|---|---|---|
| 3,796,704 | 3/1974 | Metzger et al. | 548/341 |
| 3,897,438 | 7/1975 | Draber et al. | 548/341 |
| 4,243,405 | 1/1981 | Balasubramanyan et al. | 548/341 |
| 4,415,586 | 11/1983 | Kramer et al. | 548/341 |
| 4,472,415 | 9/1984 | Worthington et al. | 548/262 |
| 4,472,421 | 9/1984 | Buchel et al. | 548/341 |
| 4,505,922 | 3/1985 | Jager et al. | 548/262 |
| 4,578,396 | 3/1986 | Jager et al. | 548/262 |
| 4,582,843 | 4/1986 | Timmler et al. | 548/262 |
| 4,634,466 | 1/1987 | Noon et al. | 548/262 |
| 4,876,354 | 10/1989 | Siegel et al. | 548/341 |

FOREIGN PATENT DOCUMENTS

| | | | |
|---|---|---|---|
| 567100 | 9/1987 | Australia | 548/341 |
| 2009020 | 11/1971 | European Pat. Off. | 548/341 |
| 0025948 | 4/1981 | European Pat. Off. | 548/341 |
| 0026856 | 4/1981 | European Pat. Off. | 514/399 |
| 0061835 | 2/1982 | European Pat. Off. | 514/399 |
| 0099165 | 1/1984 | European Pat. Off. | 548/341 |
| 0149976 | 12/1984 | European Pat. Off. | 514/389 |
| 0129798 | 1/1985 | European Pat. Off. | 548/341 |
| 0192055 | 8/1986 | European Pat. Off. | 548/341 |
| 2063857 | 7/1971 | Fed. Rep. of Germany | 548/341 |
| 2041771 | 2/1972 | Fed. Rep. of Germany | 548/341 |
| 2720868 | 11/1978 | Fed. Rep. of Germany | 514/399 |
| 2758784 | 7/1979 | Fed. Rep. of Germany | 548/262 |
| 2938597 | 4/1981 | Fed. Rep. of Germany | 548/341 |
| 3345813 | 6/1988 | Fed. Rep. of Germany | |

OTHER PUBLICATIONS

M. Ogata et al., Chemistry and Industry, 19 (1980), pp. 85 and 86.
K. H. Buchel et al., Drugs Made in Germany, vol. 15, pp. 79-94 (1972).
Chemical Abstracts 91, 57005p, 1979.
South African Patent Journal, Aug. 1986, pp. 129-130, Gerhard Walther et al., 2-(1-imidazolyl)-ethanol-derivatives, abstract of South African Patent No. 84/9745, 6/16/86.

Primary Examiner—Mary C. Lee
Assistant Examiner—Robert C. Whittenbaugh
Attorney, Agent, or Firm—Finnegan, Henderson, Farabow, Garrett and Dunner

[57] ABSTRACT

Arylmethylazoles of the formula I $$\text{Aryl} - \underset{\underset{Z \diagdown N \diagup}{\overset{R^1}{|}}}{C} - \underset{\underset{}{\overset{OR^2}{|}}}{\underset{R^3}{C}} - R^4 \quad \text{I}$$

in which
  Aryl is (substituted) phenyl or naphthyl;
  Z is CH or N;
  $R^1$ and Q are H or alkyl;
  $R^2$ is H, alk(en)yl or alkynyl;
  $R^3$ and $R^4$ are H, alkyl or other hydrocarbons; or
  $R^3$ and $R^4$ together are a —(CH$_2$)$_{2-11}$ chain or a bridged —(CH$_2$)$_{4-5}$ chain, and their acid addition salts, stereoisomers and optically active enantiomers possess outstanding antimycotic and antidepressant activity.

They are obtained, inter alia, from arylmethylazoles II $$\text{Aryl} - \underset{\underset{Z \diagdown N \diagup}{\overset{R^1}{|}}}{C} - H \quad \text{II}$$

which are reacted with a strong base and then with a carbonyl compound III O=CR$^3$R$^4$; thereafter, the product is reacted with the protic acid or with an alkyl halide IV R$^2$Hal.

If desired, the products are converted to the acid addition salts, or the stereoisomers or optically active enantiomes are resolved.

7 Claims, No Drawings

ARYLMETHYLAZOLES AND THEIR SALTS, AGENTS WHICH CONTAIN THESE COMPOUNDS, AND THEIR USE

This application is a continuation of application Ser. No. 06/909,598, filed Sept. 22, 1986, now abandoned.

The invention relates to substituted arylmethylazoles, including their salts, processes for their preparation, medicaments containing these compounds, and their use as medicaments and fungicides.

German Offenlegungsschrift 2,948,206 and European Offenlegungsschrift 61,835 state that benzylazoles are suitable for controlling fungi in humans, animals and plants. However, the activity of these compounds is unsatisfactory, particularly at low concentrations.

It is the object of the invention to provide compounds which, in addition to having a substantially improved antimycotic action, are also suitable for other indications.

The invention therefore relates to arylalkylazoles of formula I

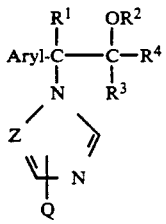

in which
aryl denotes a radical

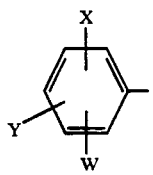

or a one- or two-naphthyl radical which is unsubstituted or substituted by U and/or a substituent V, where X denotes H ($C_1$-$C_4$)-alkyl, phenyl, fluorine, chlorine, bromine, hydroxyl, ($C_1$-$C_4$)-alkoxy,

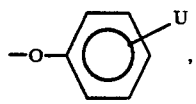

($C_1$-$C_4$)-alkylthio, —$NR_2^5$ in which the radicals $R^5$—identical or different—denote ($C_1$-$C_4$)-alkyl or together with the nitrogen atom denote a pyrrolidine, piperidine or morpholine radical, or X denotes $CF_3$ or a benzyloxy group which is unsubstituted or carries one or two substituents in the phenyl radical, the substituents being identical or different and denoting fluorine, chlorine, $OCH_3$, $OC_2H_5$ or ($C_1$-$C_3$)-alkyl, Y denotes H, ($C_1$-$C_4$)-alkyl, fluorine, chlorine, bromine, ($C_1$-$C_4$)-alkoxy or ($C_1$-$C_4$)-alkylthio, or X and Y together in the 2,3- or 3,4-position denote a —(CH$_2$)$_L$— chain, in which L=3 or 4, —O—CH$_2$CH$_2$— or —O—CH$_2$—O—, W denotes H, $CH_3$ or $OCH_3$, V denotes ($C_1$-$C_4$)-alkyl, phenyl, fluorine, chlorine, bromine, hydroxyl, ($C_1$-$C_4$)-alkoxy, ($C_1$-$C_4$)-alkylthio, —$NR_2^5$, in which $R^5$ denotes ($C_1$-$C_4$)-alkyl or together with the nitrogen atom denotes a pyrrolidine, piperidine or morpholine radical, benzyloxy or $CF_3$, and U denotes $CH_3$, F, Cl or $OCH_3$, Z denotes CH or N, $R^1$ and Q denote H or ($C_1$-$C_4$)-alkyl, $R^2$ denotes H, ($C_1$-$C_4$)-alkyl, ($C_3$-$C_5$)-alkenyl or ($C_3$-$C_5$)-alkynyl, $R^3$ and $R^4$, which are identical or different, denote H, ($C_1$-$C_{12}$)-alkyl or other hydrocarbon radicals which are unsubstituted or carry up to 3 substituents, the substituents being identical or different and denoting F, Cl, Br, ($C_1$-$C_4$)-alkoxy, $OC_6H_5$ or ($C_1$-$C_4$)-alkylthio, or $R^3$ and $R^4$ together denote a (CH$_2$)$_n$— chain which is unsubstituted or substituted by ($C_1$-$C_4$)-alkyl, $OCH_3$ or phenyl, in which n=2-11, and which contains no benzene rings or 1 or 2 benzene rings which are unsubstituted or carry up to 2 substituents, in a fused form, the substituents being identical or different and denoting F, Cl, ($C_1$-$C_4$)-alkoxy or ($C_1$-$C_4$)-alkyl, or a corresponding hydrocarbon chain containing a double bond, the hydrocarbon chain in turn containing no benzene rings or one or two benzene rings which are unsubstituted or carry up to 2 substituents, in a fused form, the substituents being identical or different and denoting F, Cl, ($C_1$-$C_4$)-alkoxy or ($C_1$-$C_4$)-alkyl, or a —(CH$_2$)$_m$— chain which is unsubstituted or substituted by ($C_1$-$C_4$)-alkyl, $OCH_3$, $CH_2OCH_3$ or phenyl and is bridged singly or multiply, in which m=4 or 5 and which contains 1 to 5 bridge carbon atoms, and the bridge carbon atoms in turn may be bridged and a bridge contains no C—C double bonds or one C—C double bond, the singly or multiply bridged —(CH$_2$)$_m$— chain containing no benzene rings or one or two benzene rings which are unsubstituted or carry up to 2 substituents, in a fused form, where the substituents are identical or different and denote F, Cl, ($C_1$-$C_4$)-alkoxy or ($C_1$-$C_4$)-alkyl, and their physiologically tolerated acid addition salts and their stereoisomers and optically active enantiomers.

Preferred compounds of the formula I are those in which at least one of the substituents has the following meaning:

Aryl denotes a radical

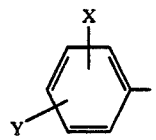

or a 2-naphthyl radical which is unsubstituted or substituted by a substituent V, in which X denotes H, ($C_1$-$C_4$)-alkyl, phenyl, F, Cl, Br, OH, ($C_1$-$C_4$)-alkoxy, 3-$CF_3$ or a benzyloxy group, Y denotes H, CH₃, Cl or OCH₃ and
V denotes $(C_1-C_4)$-alkyl, Cl, Br, OH or OCH₃,
Z denotes CH,
Q denotes H, CH₃ or C₂H₅,
$R^1$ denotes H or CH₃,
$R^2$ denotes H,
$R^3$ denotes $(C_1-C_8)$-alkyl, $(C_3-C_{10})$-alkenyl, $(C_3-C_{12})$-cycloalkyl, $(C_5-C_{12})$-cycloalkenyl, $(C_7-C_{12})$-polcycloalkyl, $(C_7-C_{12})$-polycycloalkenyl, $(C_5-C_{12})$-cycloalkyl-$(C_1-C_4)$-alkyl, $(C_5-C_{12})$-cycloalkylidene-$(C_2-C_4)$-alkyl, $(C_5-C_{12})$-cycloalkenyl-$(C_1-C_4)$-alkyl, $(C_7-C_{12})$-polycycloalkyl-$(C_1-C_4)$-alkyl $(C_7-C_{12})$-polycycloalkylidene-$(C_2-C_4)$-alkyl, $(C_7-C_{12})$-polycycloalkenyl-$(C_1-C_4)$-alkyl or these cyclic hydrocarbon radicals possessing up to 3 identical or different substituents, the latter denoting F, Cl, Br, CH₃, OCH₃ or CH₃OCH₂, or the abovementioned cyclic hydrocarbon radicals having 1 or 2 fused benzene rings which are unsubstituted or carry up to 2 substituents, the substituents being identical or different and denoting F, Cl, OCH₃, OC₂H₅ or $(C_1-C_3)$-alkyl, or a phenyl or phenyl-$(C_1-C_4)$-alkyl group which is unsubstituted or carries up to 3 substituents in the phenyl radical, the substituents being identical or different and denoting F, Cl, Br, $(C_1-C_4)$-alkoxy, $(C_1-C_4)$-alkyl, $(C_1-C_4)$-alkylthio, C₆H₅ or OC₆H₅, or a naphthyl group which is unsubstituted or carries up to 2 substituents, the substituents being identical or different and denoting F, Cl, Br, OCH₃, OC₂H₅ or $(C_1-C_3)$-alkyl $R^4$ denotes H, $(C_1-C_{12})$-alkyl, $(C_3-C_5)$-alkenyl, $(C_5-C_8)$-cycloalkyl, or a phenyl, phenyl-$(C_2-C_4)$-alkyl, naphthyl or naphthyl-$(C_1-C_4)$-alkyl group which is unsubstituted or carries up to 2 substituents in the phenyl radical or naphthyl radical, the substituents being identical or different and denoting F, Cl, Br, OCH₃, OC₂H₅ or $(C_1-C_4)$-alkyl, or $R^3$ and $R^4$ together denote a —(CH₂)$_n$— chain which is unsubstituted or substituted $(C_1-C_4)$-alkyl or phenyl, in which n=4–11 and which contains no benzene rings or 1 or 2 benzene rings which are unsubstituted or carry a substituent, in fused form, a substituent denoting F, Cl, $(C_1-C_4)$-alkoxy or $(C_1-C_4)$-alkyl, and, in the case of 2 fused benzene rings, the substituents being identical or different, or a hydrocarbon chain of this type which contains a double bond, the hydrocarbon chain again containing no benzene rings or 1 or 2 benzene rings which are unsubstituted or carry a substituent, in fused form, the substituent denoting F, Cl, $(C_1-C_4)$-alkoxy or $(C_1-C_4)$-alkyl and, in the case of 2 benzene rings, the substituents being identical or different, or a —(CH₂)$_m$— chain which is unsubstituted or substituted by CH₃, C₂H₅, OCH₃ or CH₃OCH₂ and is singly or multiply bridged, in which m=4 or 5 and which contains 1 to 5 bridge carbon atoms, where the bridge carbon atoms in turn may be bridged and a bridge contains no C—C double bonds or one C—C double bond, and the singly or multiply bridged —(CH₂)$_m$— chain contains no benzene rings or 1 or 2 benzene rings, in fused form.

Particularly preferred compounds of the formula I are those in which at least one of the substituents has the following meaning:

Aryl denotes a radical

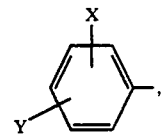

in which
X denotes $(C_1-C_4)$-alkyl, phenyl, F, Cl or $(C_1-C_4)$-alkoxy,
Y denotes H, CH₃, Cl or OCH₃ and the 6-position is always unsubstituted, or
a 2-naphthyl radical which is unsubstituted or monosubstituted by Br or Cl,
Z denotes CH, Q, $R^1$ and $R^2$ denote H,
$R^3$ denotes $(C_1-C_8)$-alkyl, $(C_5-C_7)$-cycloalkyl, $(C_7-C_{12})$-polycycloalkyl, $(C_7-C_{12})$-polycycloalkenyl, $(C_7-C_{12})$-polycycloalkyl-$(C_1-C_4)$-alkyl or the cyclic hydrocarbon radicals possessing one substituent or 1 or 2 identical or different substituents, the substituents denoting Cl, Br, CH₃ or CH₃OCH₂, or the abovementioned cyclic hydrocarbon radicals having 1 or 2 fused benzene rings,
or a phenyl or phenyl-$(C_2-C_4)$-alkyl group which is unsubstituted or carries up to 3 substituents in the phenyl radical, the substituents being identical or different and denoting F, Cl, Br, $(C_1-C_4)$-alkoxy, $(C_1-C_4)$-alkylthio, OC₆H₅ or C₆H₅ or
a naphthyl group which is unsubstituted or substituted by Cl, Br, OCH₃ or CH₃,
$R^4$ denotes H, $(C_1-C_4)$-alkyl, cyclopentyl, cyclohexyl or cyclopropyl, or
$R^3$ and $R^4$ together denote a —(CH₂)$_n$— chain which is unsubstituted or substituted by CH₃ or C₆H₅, in which n=4–11 and which does not contain any benzene rings or contains 1 or 2 benzene rings, in fused form, or
a —(CH₂)$_m$— chain which is unsubstituted or substituted by CH₃ or CH₃OCH₂ and is singly or multiply bridged, in which m=4 or 5 and which has 1 to 5 bridge carbon atoms, where the bridge carbon atoms in turn may be bridged and a bridge contains no C—C double bonds or one C—C double bond, and the singly or multiply bridged —(CH₂)$_m$— chain does not contain any benzene rings or contains 1 or 2 benzene rings, in the fused form.

Other preferred compounds of the formula I are those in which aryl denotes a radical

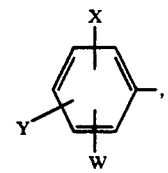

in which W denotes hydrogen and X and Y denote hydrogen, F, Cl or Br, and $R^1$ and $R^2$ denote hydrogen and $R^3$ and $R^4$ together form a (CH₂)$_n$ chain in which n=4 to 6, or $R^3$ and $R^4$ form a bridged (CH₂)$_m$ chain in which m=4 or 5 and which has 1 to 5 bridge carbon atoms, and at least one of these characteristics must be fulfilled.

In this context, the expression "$(C_1-C_3)$-, $(C_1-C_4)$-, $(C_2-C_4)$-, $(C_1-C_8)$- or $(C_1-C_{12})$-alkyl" is to be understood in each case as meaning a straight-chain or branched alkyl radical, the expression "($C_3$-$C_5$)- or ($C_3$-$C_{10}$)-alkenyl" is to be understood in each case as meaning a straight-chain or branched alkenyl radical, and the expression "($C_1$-$C_4$)-alkoxy or ($C_1$-$C_4$)-alkylthio" is to be understood as meaning a straight-chain or branched alkoxy or alkylthio radical.

The expressions "($C_5$-$C_{12}$)-cycloalkylidene-($C_1$-$C_4$)-alkyl" and "($C_7$-$C_{12}$)-polycycloalkylidene-($C_1$-$C_4$)-alkyl" are to be understood as meaning ring systems in which a ring carbon atom and a carbon atom of the straight-chain or branched ($C_1$-$C_4$)-alkyl radical are connected by a double bond.

The formula (a)-(d) below may be listed as examples of such cyclo- and polycycloalkylidene radicals.

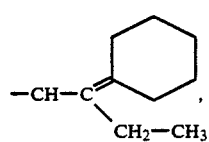
(a)

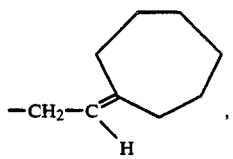
(b)

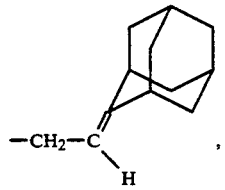
(c)

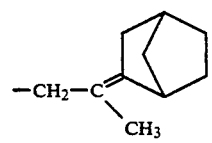
(d)

The expression "($C_7$-$C_{12}$)-polycycloalkyl" or ($C_7$-$C_{12}$)-polycycloalkenyl" is understood as meaning a polycyclic, isocyclic ring system containing 7-12 ring carbon atoms, this system containing one double bond in the case of "polycycloalkenyl". Such polycyclic ring systems are fused or bridged or both fused and bridged or spirocyclic systems. The following may be mentioned as examples of these: bicyclo[2.2.1]heptane and -heptene, bicyclo[2.2.2]-octane and -octene, tricyclo[5.2.1.0$^{2.6}$]decane and -decene, adamantane, octalin, decalin, bicyclo[4.3.0]nonane, bicyclo[3.2.1.]nonane, bicyclo[3.2.1]octane, deltacyclane (e) and spiro[4,5]decane (f)

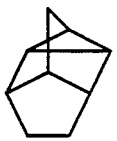
(e)

(f)

If one of the possible ring systems contains benzene rings in a fused form, then 2 carbon atoms per benzene ring are counted in the number of ring carbon atoms. The C—C double bonds inevitably introduced into the particular ring system by such fused benzene rings are not taken into account in the expression "cycloalkenyl" or "polycycloalkenyl". These expressions relate to C—C double bonds which do not belong to a benzene ring. The formulae (g) to (p) are listed, by way of illustration, as examples of such ring systems containing fused benzene rings.

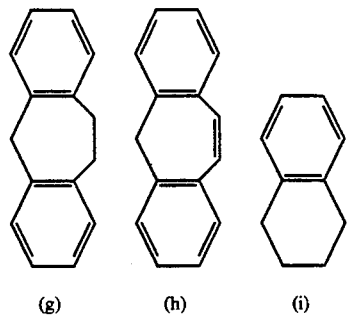
(g)   (h)   (i)

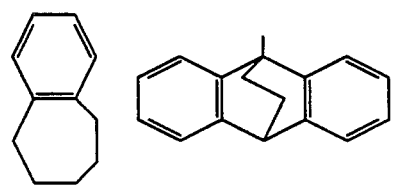
(k)   (l)

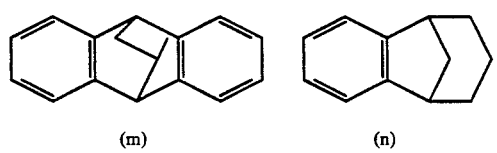
(m)   (n)

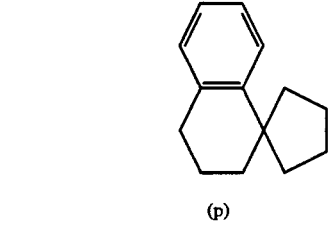
(p)

The meanings stated for "$R^3$ and $R^4$ together" designate in each case mono- or polycyclic, isocyclic ring systems to which the oxygen-carrying carbon atom in formula I belongs.

Otherwise, these ring systems are identical or analogous to those described above. Formulae (q) to (y) are listed as examples.

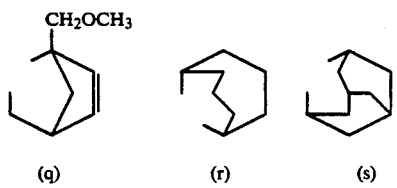
(q)   (r)   (s)

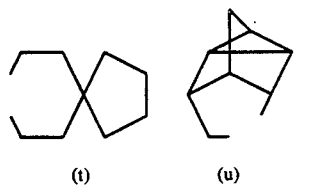
(t)   (u)

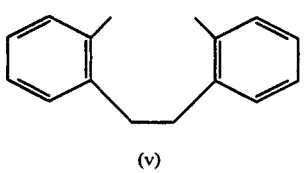

(v)

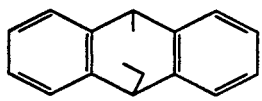

(w)

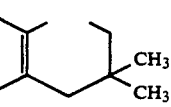

(x)

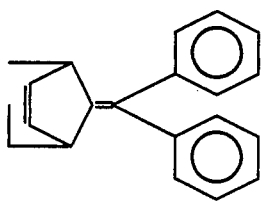

(y)

The term "hydrocarbon radicals which are unsubstituted or carry up to 3 substituents" is understood as meaning saturated or unsaturated, straight-chain or branched and/or mono- or polycyclic and/or spirocyclic hydrocarbon radicals. These may also contain fused benzene rings and, in the case of cyclic hydrocarbon radicals they may be substituted by one or more straight-chain or branched alkyl or alkenyl radicals or by one or more phenyl radicals.

Furthermore, such hydrocarbon radicals may also contain substituents which leave the character of the hydrocarbons essentially unaffected, such as, for example, F, Cl, Br or $(C_1-C_4)$-alkoxy or phenoxy groups.

The expression "unsaturated" means hydrocarbon radicals containing one or more C—C double bonds and/or C—C triple bonds.

The compounds of the formula I contain at least one asymmetric C atom, this carbon atom being the one to which the azole radical is bonded. Where $R^3$ and $R^4$ are different or together form an asymmetric ring system, the C atom carrying the oxygen is also asymmetric. Other asymmetric C atoms may be present in the radicals $R^3$ and/or $R^4$. Accordingly, the compounds I are obtained in the synthesis at least in the form of racemates. Depending on the number of asymmetry centres, stereoisomers in the form of racemates also occur. For example, in the synthesis of compounds of the formula I which, in addition to the asymmetry centre always present, contain a second one at the C atom carrying the oxygen, two diastereomer racemates may be formed in equal or different amounts. Because of stereoselectivity, such diastereomer racemates are frequently formed in different amounts, or, in an extreme case, only one is formed. The invention therefore also relates to the possible stereoisomers, in the simplest case the diastereomers, of the compounds I in the form of their racemates or in the form of the optically active enantiomers, and the optically active enantiomers of the compounds of the formula I which contain only the single asymmetry centre always present, and their pharmaceutically acceptable salts.

The compounds of the formula I can be prepared by three processes. Process a) starts from arylmethylazoles of the formula II

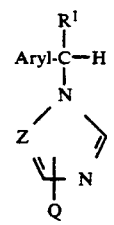

wherein aryl, Z, Q and $R^1$ have the meanings given above.

Org. React. 26, page 128 (1979) discloses that when benzylimidazole is reacted with n-butyllithium in diethyl ether at temperatures between 0° and −70° C. and carbonyl compounds are then added, only hydroxyalkylation at the imidazole ring takes place.

Arylmethylazoles can be hydroxyalkylated at the methylene group with strong bases and carbonyl compounds if more highly solvating solvents or two equivalents of a base are employed.

The process is carried out, for example, as follows: one or two equivalents of a strong base are added to an arylmethylazole of the formula II in a aprotic, advantageously polar solvent at a temperature between +40° C. and −100° C., and the product is then reacted first with a carbonyl compound of the formula III

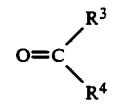

in which $R^3$ and $R^4$ have the abovementioned meanings, and then with a protic acid or an alkyl halide of the formula IV $$R^2Hal \qquad IV$$

in which $R^2$ has the meaning given above and Hal represents chlorine, bromine or iodine, to give a compound of the formula I.

Suitable strong bases are, in particular, alkali metal hydrides, such as, for example, sodium hydride, or alkaline earth metal or alkali metal alkyls, such as, for example, butyllithium, tert-butyllithium or methyllithium, phenyllithium or methylmagnesium chloride or bromide, or metallized amines, such as, for example, lithium diisopropylamide or potassium or sodium amide, lithiumalkyls, such as n-butyllithium, preferably being used.

The use of two equivalents of strong bases is appropriate for the majority of the substituents which occur according to the invention in the arylmethylimidazoles to be used as a starting material, as well as for such compounds of the formula II which are unsubstituted in the aryl radical. 1-Benzyl- and 1-naphthylimidazoles which are substituted in the phenyl or naphthyl radical by substituents with a pronounced acceptor character, such as, for example, $CF_3$, or by F, Cl and/or Br in the ortho and/or para position in the case of benzylimidazoles and in corresponding positions in the case of naphthylimidazoles constitute an exception to this rule. In these cases and in the case of the (3-chloro-phenylmethyl)-imidazoles, it is sufficient to use one equivalent of a strong base, preferably of butyllithium, in order to obtain sufficiently good yields of compounds of the formula I.

The use of two equivalents of strong bases is generally required in the case of arylmethyltriazole derivatives of the formula II (Z=N); otherwise, there is a danger that products hydroxyalkylated at the triazole ring will be obtained.

The reaction can be carried out in the solvents commonly used for organometallic reactions, such as, for example, dimethylformamide, dimethyl sulfoxide, dimethoxyethane, diethyl ether or, preferably, tetrahydrofuran. It is also possible to use mixtures of different aprotic solvents, including mixtures of polar and nonpolar solvents. Additives, such as N,N,N',N'-tetramethylethylenediamine or hexamethylphosphoric acid triamide, may also be used as solvents.

The reaction according to the invention with the strong base and with the carbonyl compound of the formula III can be carried out at temperatures between +40° and −100° C., but is preferably carried out in the range between 0° C. and −80° C. The reaction can also be effected at a temperature at above +40° C. The compounds of the formula I are isolated in a manner customary and known for organometallic reactions. The compounds of the formula I are purified, as a rule, by recrystallization from an organic solvent, such as, for example, hexane, cyclohexane, ethanol, ethyl acetate, diisopropyl ether or acetonitrile, or from a solvent mixture, or by column chromatography over silica gel.

The 1-benzylazole or azol-1-ylmethylnaphthalenes of the formula II ($R^1$=H) which are unsubstituted or substituted according to the invention in the phenyl or naphthyl radical and are used as a starting material are obtained by known methods, by alkylation of imidazole or triazole with benzyl halides or with appropriate 1- or 2-chloro- or bromoethylnaphthalenes.

Starting materials of the formula II, wherein $R^1$ denotes ($C_1$–$C_4$)-alkyl, are prepared in an analogous manner by known methods, by alkylation of imidazole or triazole with appropriate α-chloro- or α-bromoalkylbenzenes or -naphthalenes of the formula VII

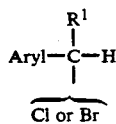

wherein aryl has the meanings given above and $R^1$ denotes ($C_1$–$C_4$)-alkyl.

The majority of the benzyl halides or chloro- or bromo-methylnaphthalenes required as starting materials are known or can be prepared by known methods, for example by reacting appropriate hydroxymethyl compounds with thionyl chloride or by brominating appropriate methyl compounds with NBS (N-bromosuccinimide). Some of the chloro- or bromoalkyl compounds of the formula VII are known or can be obtained by known methods, for example by the action of thionyl chloride on appropriate hydroxy compounds, which in turn are obtainable from the corresponding ketones by reduction with $NaBH_4$.

Process b) starts from oxiranes of the formula V

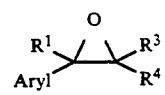

wherein aryl, $R^1$, $R^3$ and $R^4$ have the abovementioned meaning. The reaction to give compounds of the formula I is carried out, for example, by a method in which an epoxide of the formula V is subjected to a nucleophilic ring-opening reaction with a compound of the formula VI

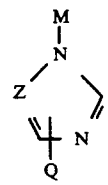

in which M denotes hydrogen or an alkali metal or alkaline earth metal and Q and Z have the meaning given above, at a temperature of between −20° C., preferably 0° C., and 150° C., preferably 60° C., preferably in a polar solvent, and the product is then reacted with a protic acid or with an alkyl halide of the formula IV.

Oxiranes of the formula V are obtained by methods known from the literature. The preparation of the parent olefins is also carried out by known methods. The oxidation of the olefins to the epoxide is effected with an organic peracid, such as, for example, peracetic acid or m-chloroperbenzoic acid, by methods known from the literature.

In process b), compounds of the formula VI, wherein M denotes Li, Na or K, in particular Na, are preferably used. The compounds of the formula VI are known or can be prepared by known methods.

In process c), for compounds of the formula I which have been prepared by process a) or b), a substituent X or V in an aryl radical of the formula I is converted to a different substituent X or V by known methods.

For example, this process c) is used to convert a benzyloxy radical in a phenyl or naphthyl group to a hydroxyl group and toluene by catalytic hydrogenolysis. Examples of suitable catalysts for this purpose are various types of finely divided palladium on active carbon or on calcium carbonate or on barium sulfate.

The reaction times are a few minutes to a few hours, depending on the process variant and on the temperature range.

From the azole derivatives of the formula I, acid addition salts can be prepared. All acids which form physiologically tolerated salts are suitable for this purpose. These include both inorganic acids and mono-, bi and trifunctional organic acids, such as, for example, hydrochloric acid, hydrobromic acid or hydroiodic acid, sulfuric acid, phosphoric acid, nitric acid, benzenesulfonic acid, toluenesulfonic acid, sulfamic acid, methylsulfuric acid, acetic acid, propionic acid, oleic acid, palmitic acid, stearic acid, malonic acid, maleic acid, succinic acid, glutaric acid, malic acid, tartaric acid, citric acid, fumaric acid, lactic acid, glycolic acid, pyruvic acid, benzoic acid, toluic acid, glutamic acid, furancarboxylic acid, salicyclic acid or mandelic acid. Salts with physiologically tolerated inorganic acids, strongly to moderately acidic derivatives of such acids or with acetic acid, succinic acid, L(+)-tartaric acid, (D)-tartaric acid, malic acid, fumaric acid, or (S)-(+)-or (R)-(−)-mandelic acid are preferred.

The compounds according to the invention, of the formula I, contain one or more asymmetry centres. If two or more asymmetry centres are present, as a rule sterioisomer mixtures are obtained in the synthesis. The individual stereoisomers may be obtained in different amounts owing to the different stereoselectivities. For example, for high stereoselectivity and in the case of diastereomers, predominantly or virtually exclusively only one diastereomers, in the form of a racemate, may be formed. Diastereomeric racemates, including diastereomers or compounds of the formula I in which, for example, an asymmetry centre is present throughout in an (R— or S—) configuration, can be resolved in a customary manner, for example by selective, fractional crystallization or column chromatography.

The diastereomeric racemates can in turn be resolved into their optical antipodes (enantiomers) in a customary manner.

The resolution of racemates and diastereomeric racemates can be carried out by methods known in principle, for example by fractional crystallization of diastereomeric salts with optically active carboxylic acids or sulfonic acids having a single configuration, or by chromatography over chiral separating media (carriers). Examples of suitable optically active, chirall acids are: L(+)- or D(−)-tartaric acid, D(+)- or L(−)-malic acid, R-(−)- or S-(+)-mandelic acid, L(+)-lactic acid, (+)-camphor-10-sulfonic acid or (+)-3-bromocamphor-8-sulfonic acid. Diastereomeric salts of such chiral acids with compounds of the formula I are subjected to fractional recrystallization from suitable solvents or solvent mixtures, until a constant angle of rotation is obtained.

By the action of an equivalent amount or an excess of base, the optically pure diastereomeric salts can be converted to the pure enantiomers of compounds I and can be isolated as such.

If, in the synthesis of compounds I by process a), carbonyl compounds of the formula III in the form of optically pure enantiomers are used, it is possible as a rule, where there is a sufficient tendency to crystallization, to resolve the resulting diastereomers into the optical antipodes without chiral auxiliaries, for example a chiral acid, in a known manner, by fractional crystallization and/or by means of chromatographic methods.

Chromatographic resolution of diastereomers or racemates over chiral carriers is possible by means of conventional column chromatography, but more effective resolution is achieved as a rule by medium pressure or high performance liquid chromatography.

The compounds of the formula I and their acid addition salts are valuable medicaments. They possess in particular an antimicrobial action and are suitable for preventing and treating fungal infections in humans and in various species of mammals. The compounds according to the invention, of the formula I, and their acid addition salts are furthermore distinguished by a powerful psychotropic, in particular antidepressant, action; they can therefore be used for the treatment of depressive states. There are effective within a broad dose range. The level of the dose administered depends on the nature of the desired treatment, on the mode of administration, and on the condition, type and size of the mammal treated. In the case of oral administration, satisfactory results are achieved with doses of from 0.1 mg, preferably from 0.4 mg, to 100 mg, preferably to 30 mg, of a compound of the formula I per kg of body weight.

The compounds of the formula (I) and their acid addition salts constitute valuable psychotropic drugs. They are very effective in the test models of a biochemical and pharmacological nature which are specific to antidepressants.

The compounds according to the invention have an antagonistic action on tetrabenazine-ptosis in the mouse and in the rat, with an $ED_{50}$ of 0.5–100 mg/kg when administered orally. The appropriate amount of a homogenate of the particular substance in aqueous carboxymethylcellulose is fed to 6 male animals by means of a gavage one hour before treatment with tetrabenazine (40 mg/kg), intraperitoneally). This pretreatment has an antagonistic effect on the tetrabenazine-ptosis.

The compounds I and their acid addition salts potentiate the toxicity of yohimbine in mice. Antidepressants of type I administered orally in a dose of 0.5 to 100 mg/kg increased the death rate for an otherwise non-fatal dose of yohimbine hydrochloride (20 mg/kg, administered subcutaneously).

An important finding is that the compounds I and their salts do not cause any stereotypes in rats and mice, even after dosages of up to 300 mg/kg, administered orally.

The antidepressant action and the usefulness for the treatment of depressive states were further demonstrated from the inhibition of the reabsorption of noradrenaline, using preparations of mouse brain synaptosomes.

The compounds and their acid addition salts are particularly valuable as a result of a structure which differs from the antidepressants known hitherto. They are equivalent or superior to known commercial products in their action and have a lower toxicity.

The compounds of the formula I furthermore possess a very good in vitro activity against skin fungi, such as, for example, *Trichophyton mentagrophytes, Microsporum canis*, or *Epidermophyton floccosum*; against molds, for example, *Aspergillus niger*, or against yeasts, such as, for example, *Candida albicans, C. tropicalis, Torulopsis glabrata* and *Trichosporon cutaneum*, or against protozoa, such as *Trichomonas vaginalis* or *T. fetus*, or against gram-positive and gram-negative bacteria.

In vivo too, for example in the experimental renal candidosis of the mouse, the compounds, after oral or parenteral administration, have a good systemic effect, for example against *Candida albicans*. There is also a very good effect against various pathogens of skin mycoses (for example *Trichophyton mentagrophytes*) in the guinea pig after oral, parenteral or, in particular, local administration.

The present invention embraces pharmaceutical formulations which, in addition to non-toxic, inert pharmaceutically suitable carriers, contain one or more active compounds according to the invention, or which consist of one or more active compounds according to the invention, and processes for the preparation of these formulations.

Non-toxic, inert pharmaceutically suitable carriers are understood as meaning solid, semisolid or liquid diluents, fillers and formulation auxiliaries of any type.

Examples of suitable administration forms of the compounds according to the invention are tablets, coated tablets, capsules, pills, aqueous solutions, suspensions and emulsions, if appropriate sterile injectable solutions, non-aqueous emulsions, suspensions and solutions, ointments, creams, pastes, lotions, sprays, etc.

The therapeutically active compounds should be present in the abovementioned pharmaceutical formulations advantageously in a concentration of about 0.01, preferably 0.10, to 99.0, preferably to 50.0, percent by weight, based on the total mixture.

The concentrations used for solutions, gels, creams or ointments and aerosols in the form of spray are in general 0.1-20, preferably 0.5-5, percent by weight.

For local administration, it is possible to use, for example, suspensions, solutions, gels, creams, ointments or suppositories.

The abovementioned pharmaceutical formulations can also contain further pharmaceutical active compounds in addition to the active compounds according to the invention.

The preparation of the abovementioned pharmaceutical formulations is carried out in a customary manner by known methods, for example by mixing the active compound or compounds with the carrier or carriers.

The present invention also embraces the use of the active compounds according to the invention and of pharmaceutical formulations which contain one or more active compounds according to the invention, in human medicine and, in the case of compounds having an antimycotic action, in human and veterinary medicine, for preventing, alleviating and/or curing the abovementioned disorders.

In the case of compounds according to the invention which have an antimycotic action, it has proven advantageous, both in human medicine and in veterinary medicine, to administer the active compound or compounds according to the invention in total amounts of about 0.05 to about 200, preferably 0.1 to 100, in particular 0.5 to 30, mg/kg of body weight every 24 hours, if appropriate in the form of several individual doses, in order to achieve the desired results. The total amount is administered in 1 to 8, preferably 1 to 3, individual doses.

The active compounds or the pharmaceutical formulations can be administered locally, parenterally, intraperitoneally and/or rectally.

The compounds of the present invention which can be used as antidepressants, and their salts, can be used for the production of pharmaceutical preparations which contain an effective amount of the active substance together with carriers and which are suitable for interal and parenteral administration. Tablets or gelatin capsules which contain the active compound together with diluents, for example lactose, dextrose, sucrose, mannitol, sorbitol, cellulose and/or glycine, and lubricants, such as silica, talc, stearic acid or its salts, such as magnesium stearate or calcium stearate and/or polyethylene glycol, are preferably used. Tablets also contain binders, such as magnesium aluminum silicate, starch, gelatin, tragacanth, methylcellulose, sodium carboxymethylcellulose and/or polyvinylpyrrolidone, and, if necessary, colorants, flavor materials and sweeteners. Injectable solutions are preferably isotonic aqueous solutions or suspensions which can be sterilized and can contain auxiliaries, such as preservatives, stabilizers, wetting agents and/or emulsifiers, solubilizers, salts for regulating the osmotic pressure and/or buffer substances. The pharmaceutical preparations according to the invention, which, if desired, can contain further pharmacologically valuable substances, are prepared, for example, by conventional mixing/granulating and coating methods and contain 0.1% to about 75%, preferably about 1% to about 50%, of the active compound.

Oral administration is effected in customary pharmaceutical formulation, for example in the form of tablets, coated tablets or capsules, which contain, for example per daily dose, 5, preferably 50, to 600 mg, preferably to 300 mg, of the active compound as a mixture with a customary carrier and/or constituents, and individual doses of 5 to 200 mg may be administered, preferably once to three times daily.

For parenteral administration, suitable suspensions or solutions can be used in a concentration of 0.1-10 percent by weight.

It may however be necessary to depart from the stated dosages and to do so as a function of the nature and body weight of the subject to be treated, the nature and severity of the disorder, the nature of the formulation and the administration of the medicament, as well as the period or interval within which administration takes place. Thus, it may be sufficient in some cases to manage with less than the abovementioned amount of active compound, whereas in other cases the abovementioned amount of active compound has to be exceeded. The particular optimum dose required and the mode of administration of the active compounds can readily be determined by any skilled worker on the basis of his specialist knowledge.

The compounds according to the invention, of the formula I, are distinguished by an outstanding fungicidal action. Fungal pathogens which have already penetrated the plant tissue can successfully be subjected to curative treatment. This is particularly important and advantageous in the case of fungal diseases which can no longer be effectively controlled with the conventional fungicides once infection has occurred. The action spectrum of the claimed compounds embraces a large number of different phytopathogenic fungi, such as, for example, *Pyricularia oryzae* or *Pellicularia sasakii*, various rust species, especially *Venturia inaequalis, Cercospora species* and powdery mildew fungi in fruit cultivation, vegetable cultivation, cereal cultivation and the cultivation of ornamentals.

The compounds of the formula I are also suitable for use in industrial areas, for example as wood preservatives, as preservatives in paints, in cooling lubricants for metal processing or as preservatives in drilling and cutting oils.

The agents can be used as wettable powders, emulsifiable concentrates, atomizable solutions, dusting agents, dressings, dispersions, granules or microgranules, in conventional formulations.

Wettable powders are preparations which can be homogeneously dispersed in water and which, in addition to the active compound and, if appropriate, a diluent or inert substance, also contain wetting agents, for example polyalkylphenols, polyoxyethylated fatty alcohols, or alkyl or alkylphenyl sulfonates, and dispersants, for example sodium ligninsulfonate, sodium 2,2'-dinaphthyl-methane-6,6'-disulfonate or sodium oleoylmethyltaurate. They are prepared in a customary manner, for example by milling and mixing the components.

Emulsifiable concentrates can be prepared, for example, by dissolving the active compound in an inert organic solvent, for example butanol, cyclohexanone, methylformamide, xylene or relative high-boiling aromatics or hydrocarbons, with the addition of one or more emulsifiers. In the case of liquid active compounds, the solvent may be completely or partly dispensed with. Examples of emulsifiers which may be used are:

Calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, fatty alcohol/propylene oxide/ethylene oxide condensation products, alkyl polyglycol ethers, sorbitan fatty acid esters, polyoxyethylene sorbitan fatty acid esters or polyoxyethylene sorbitol esters.

Dusting agents can be obtained by milling the active compound with finely divided, solid substances, for example talc or natural clays, such as kaolin, bentonite, pyrophyllite or diatomaceous earth.

Granules can be prepared either by spraying the active compound onto adsorptive, granulated inert material or by applying concentrates of the active compound by means of binders, for example polyvinyl alcohol, sodium polyacrylate or mineral oils, onto the surface of carriers, such as sand, kaolinites or granulated inert material. Suitable active compounds may also be granulated in the manner customarily used for the preparation of fertilizer granules—if desired as a mixture with fertilizers.

In wettable powders, the concentration of active compound is, for example, about 10 to 90% by weight, the remainder to 100% by weight consisting of customary formulation components. In the case of emulsifiable concentrates, the concentration of active compound can be about 10 to 80% by weight.

Dust-like formulations generally contain 5 to 20% by weight of active compound, while atomizable solutions contain about 2 to 20% by weight. In the case of granules, the content of active compound depends in part on whether the effective compound is liquid or solid and what granulation auxiliaries, fillers, etc. are used.

In addition, the stated formulations of active compounds may contain the customary adhesives, wetting agents, dispersants, emulsifiers, penetration agents, solvents, fillers or carriers.

For use, the concentrates present in commercial form are, if appropriate, diluted in a customary manner, for example, for wettable powders, emulsifiable concentrates, dispersions and, in some cases, also microgranules, by means of water. Dust-like and granulated formulations and atomizable solutions are not usually further diluted with other inert substances before being used.

Mixtures or mixed formulations with other active compounds, such as, for example, insecticides, acaricides, herbicides, fertilizers, growth regulators or fungicides, may also be possible. Particularly in the case of mixture with fungicides, synergistic increases in activity are achieved in some cases.

The examples which follow illustrate the preparation of the compounds. The reactions described in Examples 1 to 167 were carried out under a nitrogen atmosphere.

EXAMPLE 1 (COMPOUND 1)

4-Chlorophenyl-1-(1-hydroxycyclohexyl)-1-imidazolylmethane 33 ml (50 mmol) of a solution of n-butyllithium in hexane were added dropwise to a solution of 9.65 g (50 mmol) of N-(4-chlorobenzyl)-imidazole in 100 ml of tetrahydrofuran at −70° C. Stirring was continued for half an hour, after which 4.9 g (50 mmol) of cyclohexanone in 20 ml of tetrahydrofuran were added so that the temperature could be kept at −70° C. Thereafter, stirring was continued for a further hour at −70° C., the reaction mixture was allowed to warm up to room temperature in the course of one hour, water was added, and the mixture was extracted with methylene chloride. The methylene chloride phase was dried and evaporated down. 14.5 g of crude product were obtained and this product was recrystallized from 5:1 cyclohexane/ethyl acetate to give 9.3 g of a pure product of melting point 145° C.

$C_{16}H_{19}ClN_2O$ (290, 78): calculated: C 66.09, H 6.58, N 9.63%; found: C 65.90, H 6.60, N 9.40%.

EXAMPLE 2 (COMPOUND 2)

(2-Chloro-6-fluorophenyl)-1-(1-hydroxycyclopentyl)-1-imidazolylmethane 105 g (0.5 mol) of N-(2-chloro-6-fluorobenzyl)-imidazole were dissolved in 1 l of tetrahydrofuran, the solution was cooled to −78° C. and metallization was carried out at −70° C. with 320 ml (0.5 mol) of n-butyllithium in hexane. After half an hour, 42 g (0.5 mol) of cyclopentanone were added, likewise at −70° C., and the reaction mixture was allowed to warm up to room temperature in the course of three hours. Thereafter, water was added and the mixture was extracted with methylene chloride.

Evaporating down the organic phase gave 142 g of an oil from which 87 g of crystals of melting point 142° C. were obtained using 1:1 cyclohexane/ethyl acetate.

$C_{15}H_{16}ClFN_2O$ (294.76): calculated: C 61.12, H 5.47, N 9.50%; found: C 61.0, H 5.5, N 9.7%.

EXAMPLE 3 (COMPOUNDS 3a and 3b)

2,4-Dichlorophenyl-9-(9-hydroxytricycl[$5.2.1^{1.7}0^{2.6}$]-dec-3-enyl)-1-imidazolylmethane 7.4 g (50 mmol) of 9-ketotricyclo[$5.2.1^{1.7}0^{2.6}$ dec-3-ene were added slowly, at −75° C., to a solution of 11.6 g (50 mmol) of 1-imidazolyl-2,4-dichlorophenylmethyllithium in 100 ml of tetrahydrofuran, the said solution being prepared analogously to Example 1, the cooling means was removed and stirring was carried out until the reaction mixture had reached room temperature. After working up with water and methylene chloride, 18 g of crude product remained. From this product, 4.7 g of crystals of melting point 212° C. were isolated by recrystallization using 10:1 hexane/ethanol.

$C_{20}H_{20}Cl_2N_2O$ (375.29): calculated: C 64.01, H 5.37, N 7.46%; found: C 64.0, H 5.3, N 7.3%.

Evaporating down the mother liquor and boiling the residue with isopropanol ether gave 7.3 g of a second isomer of melting point 150° C.

$C_{20}H_{20}Cl_2N_2O$ (375.29): calculated: C 64.01, H 5.37, N 7.46%; found: C 63.5, H 5.7, N 7.2%.

EXAMPLE 4 (COMPOUND 4)

1-(4-Biphenyl)-3,3-dimethyl-1-(1-imidazolyl)-butan-2-ol 2.6 g (50 mmol) of pivalaldehyde in 20 ml of tetrahydrofuran were slowly added dropwise, at −70° C., to a solution of 7.2 g (50 mmol) of 1-imidazolyl-4-biphenylmethyllithium in 100 ml of tetrahydrofuran, the said solution being prepared in analogy to Example 1, and the mixture was allowed to warm up to room temperature. Working up with water/methylene chloride gave 9.4 g of an oil, from which 4.8 g of a product of melting point 166° C. were obtained after recrystallization with 1:1 cyclohexane/ethyl acetate.

$C_{21}H_{24}N_2O$ (320.42): calculated: C 78.72, H 7.55, N 8.74%; found: C 78.5, H 7.5, N 8.6%.

EXAMPLE 5 (COMPOUND 5)

2-Allyloxy-2-cyclohexyl-1-(2,4-dichlorophenyl)-1-(1-imidazolyl)-ethane 33 ml (50 mmol) of n-butyllithium in hexane were added to 11.4 g (50 mmol) of N-(2,4-dichlorobenzyl)-imidazole in 100 ml of tetrahydrofuran at $-78°$ C., stirring was continued for half an hour and 6.1 g (55 mmol) of hexahydrobenzaldehyde were then added dropwise. The mixture was kept at $-70°$ C. for a further two hours, after which it was allowed to warm up to 0° C. and 6.7 g (55 mmol) of allyl bromide in 50 ml of tetrahydrofuran were added. The reaction mixture was then stirred for 15 hours at room temperature and worked up with water/methylene chloride. 19.8 g of a crude product were obtained in the form of an oil, from which 5.5 g of the imidazole derivative were isolated by column chromatography over silica gel using 4:1 cyclohexane/ethyl acetate.

$C_{20}H_{24}Cl_2N_2O$ (379.32): calculated: C 63.33, H 6.38, N 7.38%; found: C 63.5, H 6.7, N 6.7%.

EXAMPLE 6 (COMPOUND 6)

1-Cyclohexyl-2-(2,4-dichlorophenyl)-2-(1-imidazolyl)-propan-1-ol

A solution of 12.4 g (50 mmol of 1-(1-imidazolyl)-1-(2,4-dichlorophenyl)-ethyllithium was prepared analogously to Example 1, and 5.6 g (50 mmol) of cyclohexanal were added dropwise at $-70°$ C. Stirring was carried out for a further 2 hours at $-70°$ C., and the mixture was allowed to reach room temperature and worked up with water/methylene chloride. After the organic phase has been evaporated down, 18 g of an oil remained, from which 4.1 g of product were isolated in the form of an oil by column chromatography over silica gel using 2:1 cyclohexane/ethyl acetate.

$C_{18}H_{22}Cl_2N_2O$ (353.28): calculated: C 61.20, H 6.27, N 7.92%; found: C 61.2, H 6.2, N 7.7%.

EXAMPLE 7 (COMPOUND 7)

2-Bromophenyl-1-(1-hydroxycycloheptyl)-1-imidazolylmethane

A solution of lithium diisopropylamide in 100 ml of tetrahydrofuran was prepared at $-30°$ C. from 5.1 g (50 mmol) of diisopropylamine and 30 ml (50 mmol) of n-butyllithium in hexane. 11.85 g (50 mmol) of N-(2-bromobenzyl)-imidazole were added dropwise to this solution at $-78°$ C., stirring was carried out for half an hour and 5.6 g (50 mmol) of cycloheptanone were then added at this temperature. The reaction mixture was warmed up to room temperature in the course of 3 hours and worked up with water and methylene chloride. 12 g of crude product were obtained, and this product gave 5.5 g of an imidazole derivative of melting point 108° C. after recrystallization with cyclohexane/ethyl acetate.

EXAMPLE 8 (COMPOUND 8)

1-(1-Hydroxycycloheptyl)-1-imidazolyl-phenylmethane 7.9 g (50 mmol) of N-benzylimidazole were dissolved in 150 ml of tetrahydrofuran, 6.0 g (50 ml) of N,N,N',N'-tetramethylethylenediamine were added and the mixture was cooled to $-78°$ C. Thereafter, 66 ml (100 mmol) of n-butyllithium in hexane were added so that the temperature of the reaction mixture did not exceed $-50°$ C. Stirring was carried out for a further 20 minutes at $-70°$ C., 5.6 g of cycloheptanone were added dropwise and the mixture was allowed to warm up to room temperature. After working up with water/methylene chloride and recrystallization with ethyl acetate, 5.8 g of crystals of melting point 175° C. were obtained.

$C_{17}H_{22}N_2O$ (270.36): calculated: C 75.52, H 8.20, N 10.36%; found: C 75.8, H 8.6, N 10.1%.

EXAMPLE 9 (COMPOUND 9)

2-Chlorophenyl-2-(2-hydroxyadamantyl)-1-(1,2,4-triazolyl)-methane 66 ml (100 mmol) of n-butyllithium in hexane were added dropwise, at $-78°$ C., to a solution of 9,7 g (50 mmol) of 1-(2-chlorobenzyl)-1,2,4-triazole and 6 g (50 mmol) of N,N,N',N'-tetramethylethylenediamine in 100 ml of tetrahydrofuran, stirring was carried out for a further half an hour at this temperature and 7.5 g (50 mmol) of adamantanone in tetrahydrofuran were then added so that $-70°$ C. was not exceeded. The reaction mixture was kept at $-78°$ C. for a further 2 hours and then allowed to warm up to room temperature. After working up with water/methylene chloride, 17.4 g of crude product were obtained, and this product gave 10.0 g of pure triazole derivative of melting point 178° C. after recrystallization from ethyl acetate.

$C_{19}H_{22}ClN_3O$ (343.86): calculated: C 66.37, H 6.45, N 12.22%; found: C 66.8, H 6.6, N 11.8%.

EXAMPLE 10 (COMPOUND 10)

2,4-Dichlorophenyl-1-(1-hydroxycyclopentyl)-1-(1,2,4-triazolyl)-methane 11.4 g (50 mmol) of 1-(2,4-dichlorobenzyl)-1,2,4-triazole were dissolved in 100 ml of tetrahydrofuran, and metallized at $-50°$ C. with 66 ml (100 mmol) of n-butyllithium in hexane. After 30 minutes, 4.2 g (50 mmol) of cyclopentanone were added, likewise at $-50°$ C., stirring was carried out for a further hour and the mixture was then slowly warmed up to room temperature. Working up with water/methylene chloride gave 14 g of an oil, from which 7.4 g of crystals of melting point 110° C. were obtained by boiling up with ethyl acetate.

$C_{14}H_{15}Cl_2N_3O$ (312.21): calculated: C 53.86, H 4.84, N 13.46%; found: C 54.2, H 5.1, N 13.2%.

The following compounds of the formula I in which Z=CH and Q=H, were obtained analogously to Examples 1-10:

TABLE 1

| Example No. | Aryl | $R^1$ | $R^2$ | $R^3$ | $R^4$ | M.p. [°C.] |
|---|---|---|---|---|---|---|
| 11 | 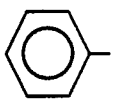 | H | H | | —(CH$_2$)$_5$— | 148 |

TABLE 1-continued
| Example No. | Aryl | R¹ | R² | R³ | R⁴ | M.p. [°C.] |
|---|---|---|---|---|---|---|
| 12 | 4-Cl-C₆H₄ 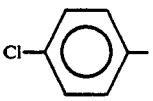 | H | H | CH₃ | —(CH₂)₄CH₃ | 148 |
| 13 | 4-Cl-C₆H₄ 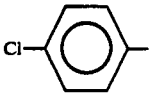 | H | H | CH₃ | —CH₂—CH(CH₃)₂ | (A)*) 159 (B) 130 |
| 14 | 4-Cl-C₆H₄ 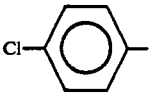 | H | H | H | —C(CH₃)₃ | amorphous |
| 15 | 4-Cl-C₆H₄ 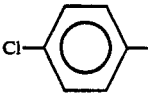 | H | H | —(CH₂)₄— | | 127 |
| 16 | 4-Cl-C₆H₄ 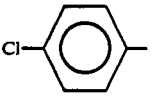 | H | H | —(CH₂)₆— | | 151 |
| 17 | 4-Cl-C₆H₄ 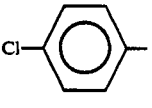 | H | H | —(CH₂)₁₁— | | 176 |
| 18 | 4-Cl-C₆H₄ 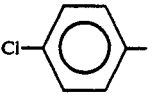 | H | H | cyclopentane-1,2-diyl-bis(methylene) | | 118 |
| 19 | 4-Cl-C₆H₄ 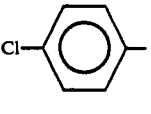 | H | H | cyclohexane-1,2-diyl-bis(methylene) | | 168 |
| 20 | 4-Cl-C₆H₄ 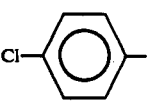 | H | H | bicyclic bridged diyl | | 240 |
| 21 | 3-Cl-C₆H₄ 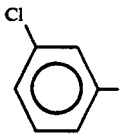 | H | H | —(CH₂)₄— | | 137 |
| 22 | 3-Cl-C₆H₄ 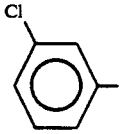 | H | H | —(CH₂)₅— | | 184 |

TABLE 1-continued

| Example No. | Aryl | R¹ | R² | R³ | R⁴ | M.p. [°C.] |
|---|---|---|---|---|---|---|
| 23 | 2,3-dichlorophenyl (Cl at 1,2) | H | H | —(CH₂)₆— | | 100 |
| 24 | dichlorophenyl | H | H | —(CH₂)₁₁— | | 186 |
| 25 | dichlorophenyl | H | H | bicyclic —CH—CH₂—CH₂—CH—CH₂—CH— bridge | | 184 |
| 26 | dichlorophenyl | H | H | H | —C(CH₃)₃ | 176 |
| 27 | chlorophenyl | H | H | H | —C(CH₃)₃ | 110 |
| 28 | chlorophenyl | H | H | H | —CH(CH₃)₂ | 168 |
| 29 | chlorophenyl | H | H | —(CH₂)₄— | | oil |
| 30 | chlorophenyl | H | H | —(CH₂)₅— | | 108 |
| 31 | chlorophenyl | H | H | —(CH₂)₆— | | 136 |
| 32 | chlorophenyl | H | H | —CH₂—CH₂—CH(C₆H₅)—CH₂—CH₂— | | 174 |

TABLE 1-continued

| Example No. | Aryl | R¹ | R² | R³ | R⁴ | M.p. [°C.] |
|---|---|---|---|---|---|---|
| 33 | 2-Cl-C₆H₄ | H | H | $-CH_2-CH_2-$<br>$\phantom{-CH_2-}CH-CH_3$<br>$-CH_2-CH_2-$ | | 162 |
| 34 | 2-Cl-C₆H₄ | H | H | $-CH_2-CH_2-$<br>$\phantom{-CH_2-}CH-C(CH_3)_3$<br>$-CH_2-CH_2-$ | | amorphous |
| 35 | 2-Cl-C₆H₄ | H | H | $-CH_2-CH(CH_3)$<br>$\phantom{-CH_2-CH(}CH_2$<br>$-CH_2-CH_2$ | | 116 |
| 36 | 2-Cl-C₆H₄ | H | H | $-CH_2-CH_2-$<br>$\phantom{-CH_2-}CH_2$<br>$-CH(CH_3)-CH_2$ | | 172 |
| 37 | 2-Cl-C₆H₄ | H | H | (decahydronaphthalene-2,3-diyl) | | amorphous |
| 38 | 2-Cl-C₆H₄ | H | H | (cyclopentane-1,3-diyl with CH₂) | | 178 |
| 39 | 2-Cl-C₆H₄ | H | H | (bicyclic CH bridge) | | 138 |
| 40 | 2-Cl-C₆H₄ | H | H | (bicyclic ring system) | | 244 |
| 41 | 2-Br-C₆H₄ | H | H | $-(CH_2)_6-$ | | 108 |
| 42 | 2-Br-C₆H₄ | H | H | $-(CH_2)_4-$ | | |

TABLE 1-continued
| Example No. | Aryl | R¹ | R² | R³ | R⁴ | M.p. [°C.] |
|---|---|---|---|---|---|---|
| 43 | 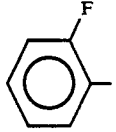 | H | H | —(CH₂)₅— | | 130 |
| 44 | 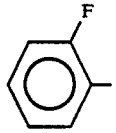 | H | H | —(CH₂)₆— | | 142 |
| 45 | 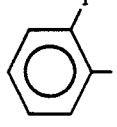 | H | H | 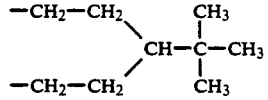 | | amorphous |
| 46 | 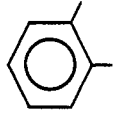 | H | H | 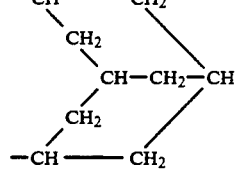 | | 253 |
| 47 | 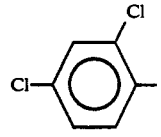 | H | H | H | 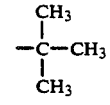 | 182 |
| 48 | 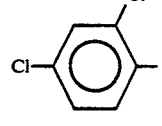 | H | H | H |  | 159 |
| 49 | 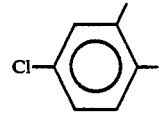 | H | H | 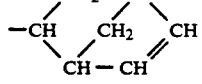 | H | 184 |
| 50 | 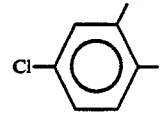 | H | H | —(CH₂)₄— | | 128 |
| 51 | 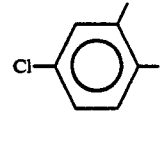 | H | H | —(CH₂)₅— | | 192 |
| 52 | 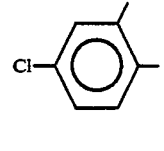 | H | H | —(CH₂)₆— | | 137 |

TABLE 1-continued

| Example No. | Aryl | R¹ | R² | R³ | R⁴ | M.p. [°C.] |
|---|---|---|---|---|---|---|
| 53 | 2,4-dichlorophenyl | H | H | —(CH₂)₁₁— | | 170 |
| 54 | 2,4-dichlorophenyl | H | H | —CH(CH₂CH₂—)(CH₂CH₂—)—phenyl | | 140 |
| 55 | 2,4-dichlorophenyl | H | H | adamantyl-type (bicyclic CH₂/CH structure) | | amorphous |
| 56 | 2,4-dichlorophenyl | H | H | cyclopentane-1,3-diyl-bis(methylene) | | 158 |
| 57 | 2,4-dichlorophenyl | H | H | bicyclic CH/CH₂ structure | | 173 |
| 58 | 2,4-dichlorophenyl | H | H | bicyclic CH/CH₂ structure (larger) | | 180 |
| 59 | 2,4-dichlorophenyl | H | H | H | CH₃ | oil |
| 60 | 2,4-dichlorophenyl | H | H | H | cyclohexyl | 130° |
| 61 | 2,4-dichlorophenyl | H | CH₂—CH=CH₂ | H | —CH₃ | oil |
| 62 | 2,6-dichlorophenyl | H | H | H | —C(CH₃)₃ | 174 |

TABLE 1-continued

| Example No. | Aryl | R¹ | R² | R³ | R⁴ | M.p. [°C.] |
|---|---|---|---|---|---|---|
| 63 | 2,3-dichlorophenyl | H | H | —(CH$_2$)$_5$— | | 181 |
| 64 | 2,3-dichlorophenyl | H | H | bicyclic -CH$_2$-CH / CH$_2$-CH$_2$ / -CH-CH$_2$ | | 174 |
| 65 | 2,3-dichlorophenyl | H | H | bicyclic -CH$_2$-CH / CH$_2$-CH-CH$_2$ / -CH-CH$_2$-CH$_2$ | | 248 |
| 66 | 2,3-dichlorophenyl | H | H | bicyclic -CH-CH$_2$ / CH$_2$-CH-CH$_2$-CH / -CH-CH$_2$ | | 240 |
| 67 | 2-chloro-6-fluorophenyl | H | H | —(CH$_2$)$_5$— | | 170 |
| 68 | 2-chloro-4-fluorophenyl | H | H | —(CH$_2$)$_6$— | | 134 |
| 69 | 2-chloro-6-fluorophenyl | H | H | bicyclic -CH$_2$-CH / CH$_2$-CH-CH$_2$ / -CH-CH$_2$-CH$_2$ | | 182 |
| 70 | 2-chloro-6-fluorophenyl | H | H | bicyclic -CH-CH$_2$ / CH$_2$-CH-CH$_2$-CH / -CH-CH$_2$ | | 200 |

TABLE 1-continued

| Example No. | Aryl | R¹ | R² | R³ | R⁴ | M.p. [°C.] |
|---|---|---|---|---|---|---|
| 71 | 2-Cl, 4-F-phenyl | H | H | H | —C(CH₃)₃ | 200 |
| 72 | 3-Cl, 4-F-phenyl | H | H | —(CH₂)₅— | | 158 |
| 73 | 3-Cl, 4-F-phenyl | H | H | —CH₂—CH₂—CH(—CH₂—CH₂—)C(CH₃)₃ | | 164 |
| 74 | 3-Cl, 4-F-phenyl | H | H | —CH₂—CH(—CH₂—CH(—CH₂—CH₂—)CH—)CH— (bicyclic) | | amorphous |
| 75 | biphenyl-4-yl | H | H | —(CH₂)₄— | | 162 |
| 76 | biphenyl-4-yl | H | H | —(CH₂)₅— | | 130 |
| 77 | biphenyl-4-yl | H | H | —(CH₂)₆— | | 182 |
| 78 | biphenyl-4-yl | H | H | —CH₂—CH₂—CH(—CH₂—CH₂—)CH(—CH₂—CH₂—)— (cycloheptyl-type) | | 180 |
| 79 | biphenyl-4-yl | H | H | —CH₂—CH(—CH₂—CH₂—)CH₂—CH— (cyclopentyl-type) | | 200 |
| 80 | biphenyl-4-yl | H | H | —CH₂—CH(—CH₂—CH(—CH₂—CH₂—)CH—)CH— (bicyclic) | | 180 |

TABLE 1-continued

| Example No. | Aryl | $R^1$ | $R^2$ | $R^3$ | $R^4$ | M.p. [°C.] |
|---|---|---|---|---|---|---|
| 81 | biphenyl-4-yl | H | H | bicyclic CH-CH₂/CH₂/CH-CH₂-CH/CH₂/CH-CH₂ structure | | 237 |
| 82 | naphthalen-2-yl | H | H | $-(CH_2)_5-$ | | 194 |
| 83 | naphthalen-2-yl | H | H | $-(CH_2)_6-$ | | 166 |
| 84 | naphthalen-2-yl | H | H | $-(CH_2)_4-$ | | 167 |
| 85 | naphthalen-2-yl | H | H | $-CH_2-CH$ with $CH_2$, $CH$, $CH_2$, $-CH-CH$, $CH_2$, $CH_2$ ring | | 184 |
| 86 | phenyl | H | H | as for Example 81 | | 216 |
| 87 | 3,4-dichlorophenyl | H | H | as for Example 81 | | 208 |

The following substances of the formula I, in which Z = N and Q = H, were obtained analogously to Examples 9 and 10:

| 88 | 2-chlorophenyl | H | H | $-(CH_2)_4-$ | | oil |
| 89 | 2-chlorophenyl | H | H | $-(CH_2)_5-$ | | oil |

TABLE 1-continued

| Example No. | Aryl | R¹ | R² | R³ | R⁴ | M.p. [°C.] |
|---|---|---|---|---|---|---|
| 90 | 2-Cl-phenyl | H | H | H | −C(CH₃)₃ | 124 |
| 91 | 2-Cl-phenyl | H | H | −CH₂−CH₂, −CH₂−CH₂ \ CH−C(CH₃)₃ | | amorphous |
| 92 | 2,4-diCl-phenyl | H | H | H | −C(CH₃)₃ | oil |
| 93 | 2,4-diCl-phenyl | H | H | H | −CH(CH₃)₂ | amorphous |
| 94 | 2,4-diCl-phenyl | H | H | −(CH₂)₅− | | oil |
| 95 | 2,4-diCl-phenyl | H | H | −CH₂−CH₂, −CH₂−CH₂ \ CH−CH₃ | | amorphous |
| 96 | 2-Cl-6-F-phenyl | H | H | −(CH₂)₄− | | 148 |
| 97 | 2-Cl-6-F-phenyl | H | H | −(CH₂)₅− | | 141 |
| 98 | 2,6-diCl-phenyl | H | H | −(CH₂)₅− | | 160 |

*)Diastereomers

EXAMPLE 99

Preparation of the starting material 1-(2,4-dichlorobenzyl)-1,2,4-triazole 34.5 g (0.5 mol) of triazole in 400 ml of dimethylformamide were initially taken, and 15.0 g (0.5 mol) of 80% strength sodium hydride were then added slowly. After the solution had become clear, 2,4-dichlorobenzyl chloride was added dropwise at 35°–45° C., and the mixture was stirred for 4 hours at 80° C., poured onto ice water and extracted with methylene chloride. After the methylene chloride phase had been evaporated down, 125 g of residue remained, and this was recrystallized from hexane/ethyl acetate. 98 g of the triazole derivative of melting point 67° C. were obtained.

EXAMPLE 100 (COMPOUND 100)

3-Fluorophenyl-(2-hydroxy-2-adamantyl)-1-imidazolylmethane 55 ml (85 mmol) of a 1.55 molar solution of n-butyllithium in hexane were added dropwise to a solution of 7.04 g (40 mmol) of N-(3-fluorobenzyl)-imidazole and 4.65 g (40 mmol) of N,N,N',N'-tetramethylethylenediamine (TMEDA) in 90 ml of absolute tetrahydrofuran (THF) at −70° C. The mixture was stirred for a further 20 minutes at −70° C., and a solution of 6.01 g (40 mmol) of adamantanone in 30 ml of absolute tetrahydrofuran (THF) was then added dropwise at −70° C. in the course of about 15 minutes. Stirring was then continued for 15 minutes at about −70° C., the reaction mixture was allowed to warm up to room temperature in the course of about 2 hours, 200 ml of water were added at about 5°-18° C., while cooling, and the mixtures was extracted with $CH_2Cl_2$. The combined $CH_2Cl_2$ extracts were dried, filtered, and evaporated down in vacuo. The residue of the extract was dissolved in acetonitrile, after which crystalline 3-fluorophenyl-(2-hydroxy-2-adamantyl)-imidazolylmethane was precipitated in pure form. After the crystalline product had been filtered off under suction and washed thoroughly with acetonitrile, 8.70 g of pure product of melting point 191° C. were obtained.

$C_{20}H_{23}FN_2O$ (326.42): calculated: C 73.59, H 7.10, F 5.82, N 8.58%; found: C 73.5, H 7.2, F 5.8, N 8.6%.

EXAMPLE 101 (COMPOUND 101)

3-Methoxyphenyl-(2-hydroxy-2-adamantyl)-1-imidazolylmethane 55 ml (85 mmol) of a 1.55 molar solution of n-butyllithium in hexane were added dropwise to a solution of 7.52 g (40 mmol) of N-(3-methoxybenzyl)-imidazole and 4.65 g (40 mmol) of TMEDA in 90 ml of absolute THF at −70° C. The mixture was stirred for a further 20 minutes at −70° C., and a solution of 6.01 g (40 mmol) of adamantanone in 30 ml of absolute THF was then added dropwise at −70° C. in the course of about 10 minutes. The procedure was then continued as described in Example 100. The residue (13 g) from the $CH_2Cl_2$ extract was crystallized from acetonitrile. 7.5 g of pure 3-methoxyphenyl-(2-hydroxy-2-adamantyl)-1-imidazolylmethane of melting point 182° C. were obtained.

$C_{21}H_{26}N_2O_2$ (338.46): calculated: C 74.52, H 7.74, N 8.28%; found: C 74.5, H 7.7, N 8.4%.

EXAMPLE 102 (COMPOUND 102)

1-(3-Chlorophenyl)-1-(2-hydroxy-2-adamantyl)-1-(1-imidazolyl)-ethane 36 ml (54 mmol) of a 1.5 molar solution of n-butyllithium in hexane were added dropwise to a solution of 5.37 g (26 mmol) of 1-(3-chlorophenyl)-1-(1-imidazolyl)-ethane and 3.14 g (27 mmol) of TMEDA in 60 ml of absolute THF at −70° C. The mixture was stirred for 20 minutes at −70° C., after which a solution of 3.91 g of adamantone in 20 ml of absolute THF was added dropwise at −70° C. Stirring was continued for 1 hour at −70° C. and for 1.5 hours at −70° C. to room temperature, 100 ml of water were added at about 10° C., while cooling, and the mixture was extracted with $CH_2Cl_2$. The combined $CH_2Cl_2$ extracts were dried and filtered and then evaporated down in vacuo. The residue (10.1 g) was chromatographed with elution with $CH_2Cl_2/C_2H_5OH$ mixtures having an increasing $C_2H_5O$ content (up to a maximum of 2% by volume), over a silica gel S/$CH_2Cl_2$ column (diameter 2.0 cm, height 41 cm). After elution of 3.3 g of unchanged adamantone ($=84\%$ of the amount used), a fraction (about 1.0 g) enriched with the desired compound was obtained during elution with $CH_2Cl_2$. This fraction was chromatographed again over the silica gel S column (diameter 2.0 cm, height 34 cm) using 4:1 petroleum ether/$CH_2Cl_2$, elution being carried out with petroleum ether/$CH_2Cl_2$ mixtures having an increasing $CH_2Cl_2$ content and then with $CH_2Cl_2$. After elution of preliminary zones (content 0.25 g), fractions shown to be pure by linear chromatography were combined and evaporated down in vacuo. 0.58 g ($=6.3\%$ yield) of pure 1-(3-chlorophenyl)-1-(2-hydroxy-2-adamantyl)-1-(1-imidazolyl)-ethane of melting point 121° C. (from $CH_3CN$) was obtained.

$C_{21}H_{25}ClN_2O$ (356.90): calculated: C 70.67, H 7.06, N 7.85, O 4.48%; found: C 72.5, H 7.0, N 7.8, O 4.4%.

EXAMPLE 103 (COMPOUND 103)

(3-Trifluoromethylphenyl)-(2-hydroxy-2-adamantyl)-1-imidazolylmethane 13.5 ml (20 mmol) of a 1.5 molar solution of n-butyllithium in hexane were added dropwise to a solution of 4.80 g (20 mmol) of 95% strength N-(3-trifluoromethylbenzyl)-imidazole in 40 ml of absolute THF at −70° C. After 45 minutes at −70° C., a solution of 3.03 g of adamantanone in 16 ml of absolute THF was added dropwise at −40° C. The mixture was stirred for 1 hour at about −40° C., for 45 minutes at −40° C. to 0° C., for 20 minutes at 0° C. to room temperature and 2 hours at about 20° C., 300 ml of water were added at about 10° C. while cooling, and the mixture was extracted with $CH_2Cl_2$. The combined $CH_2Cl_2$ extracts were dried and filtered and then evaporated down in vacuo. The residue (7.3 g) crystallized on dissolving in acetonitrile. After the crystals had been filtered off under suction and washed thoroughly with $CH_3CN$ and dried, 2.10 g of pure crystalline product of melting point 233° C. were obtained. The mother liquor residue (5.2 g) was chromatographed over a silica gel S/$CH_2Cl_2$ column (diameter 2.1 cm, height 34 cm), with elution with $CH_2Cl_2$ and $CH_2Cl_2/C_2H_5OH$ mixtures (up to a maximum of 2% by volume of $C_2H_5OH$). Combined pure fractions gave a further 0.50 g of (3-trifluoromethylphenyl)-2-hydroxy-2-adamantyl)-1-imidazolylmethane of melting point 232° C. after crystallization from $CH_3CN$.

$C_{21}H_{23}F_3N_2O$ (376.43): calculated: C 67.01, H 6.16, F 15.14, N 7.44%; found: C 66.9, H 6.1, F 15.2, N 7.3%.

EXAMPLE 104 (COMPOUND 104)

(3-Dimethylaminophenyl)-(2-hydroxy-2-adamantyl)-1-imidazolylmethane 20 ml (31 mmol) of a 1.55 molar solution of n-butyllithium in hexane were added dropwise to a solution of 3.03 g (15 mmol) of (3-dimethylaminobenzyl)-imidazole and 1.75 g (15 mmol) of TMEDA in 30 ml of absolute THF. Stirring was carried out for 1 hour at −70° C., after which a solution of 2.26 g of adamantanone in 40 ml of absolute THF was added dropwise at −30° to −15° C. The mixture was allowed to warm up to room temperature in the course of about 45 minutes and was stirred for a further 2 hours at room temperature, 400 ml of water were added at 10° C., while cooling, and stirring was continued for 15 minutes at 0°-5° C., a crystalline precipitate being formed. This was filtered off under suction, rinsed with hexane and diisopropyl ether and dried in vacuo. 2.20 g (=41.7% yield) of pure (3-dimethylaminophenyl)-(2-hydroxy-2-adamantyl)-1-imidazolylmethane of melting point 185° C. were obtained.

$C_{22}H_{29}N_3O$ (351.50): calculated: C 75.18, H 8.32, N 11.96%; found: C 75.0, H 8.5, N 11.8%.

EXAMPLE 105 (COMPOUND 105)

1-(1-Adamantyl)-2-(3-chlorophenyl)-2-(1-imidazolyl)-ethanol 15.5 ml (23 mmol) of a 1.5 molar solution of n-butyllithium in hexane were added dropwise to a solution of 3.85 g (20 mmol) of N-(3-chlorobenzyl)-imidazole in 46 ml of absolute THF at −70° C. The mixture was stirred for 30 minutes at −70° C., after which a solution of 3.20 g (20 mmol) of 1-formyladamantane in 20 ml of absolute THF was added dropwise at −70° C. Stirring was continued for 1 hour at about −70° C. and for 2 hours at about −70° C. to room temperature, 120 ml of water were added at about 10° C., while cooling, and the suspension formed was stirred for 1.5 hours at 5°-8° C. Thereafter, the crystalline substance (crude product) was filtered off under suction and rinsed with water and hexane, and the crystalline product, dissolved in $CH_2Cl_2$, was filtered over a silica gel/$CH_2Cl_2$ column (diameter 2.0 cm, height 20 cm). The filtered solution was evaporated down in vacuo and the residue (2.36 g) was crystallized from acetone. 2.15 g (=30.1% yield) of pure 1-(1-adamantyl)-2-(3-chlorophenyl)-2-(1-imidazolyl)-ethanol of melting point 115° C. were obtained.

$C_{21}H_{25}ClN_2O$ (356.90): calculated: C 70.67, H 7.06, Cl 9.93, N 7.85%; found: C 70.2, H 7.1, Cl 10.0, N 7.7%.

EXAMPLE 106 (COMPOUND 106)

(2-Hydroxy-2-adamantyl)-1-imidazolyl-(3-tolyl)-methane 39 ml (60.5 mmol) of 1,55 molar n-butyllithium/hexane solution were added dropwise to a solution of 5.17 g (30 mmol) of N-(3-methylbenzyl)-imidazole and 3.49 g (30 mmol) of TMEDA in 60 ml of absolute THF at −70° C. The mixture was stirred for 30 minutes at −70° C., after which a solution of 4.51 g of adamantanone in 35 ml of absolute tetrahydrofuran was added dropwise at about −70° C., stirring was continued for 20 minutes at −70° C., the mixture was allowed to warm up to room temperature, 300 ml of water were added, while cooling, and the mixture was then stirred for 15 minutes at about 5° C. Thereafter, the crystalline substance which had separated out was filtered off with suction, rinsed with water and hexane, dried and boiled up with about 25 ml of $CH_3CN$ for 3 minutes. After cooling, the solid was again filtered off under suction and dried. 3.87 g (=40% yield) of pure (2-hydroxy-2-adamantyl)-1-imidazolyl-(3-tolyl)-methane of melting point 186° C. were obtained.

$C_{21}H_{26}N_2O$ (322.46): calculated: C 78.22, H 8.13, N 8.69%; found: C 78.0, H 8.2, N 8.5%.

EXAMPLE 107 (COMPOUNDS 107a, 107b, 107c and 107d)

1-(3-chlorophenyl)-1-(1-imidazolyl)-nona-3,7-dien-2-ol 26 ml (40 mmol) of 1.55 molar n-butyllithium/hexane solution were added dropwise to a solution of 7.70 g (40 mmol) of N-(3-chlorobenzyl)-imidazole in 100 ml of absolute THF at −70° C. in the course of 15 minutes. The mixture was stirred for 30 minutes at −70° C., after which a solution of 6.10 g (40 mmol) of citral (cis/trans mixture) in 50 ml of absolute THF was added dropwise at −70° C., stirring was continued for 45 minutes at about −70° C., the mixture was allowed to warm up to room temperature in the course of about 2 hours, 300 ml of water were added, while cooling, and the mixture was extracted with $CH_2Cl_2$. The combined $CH_2Cl_2$ extracts were dried, filtered and evaporated down in vacuo. The residue (13.2 g) from the extract was chromatographed over a silica gel S/n-hexane column (diameter 2.5 cm, height 56 cm), with elution with hexane/ethanol mixtures having an increasing ethanol content (up to a maximum of 20% of ethanol). The course of the elution was monitored by means of thin layer chromatography. This showed that the desired compound was present in the form of 4 stereoisomers in similar amounts. Fractions which were shown to be pure by thin layer chromatography were combined and evaporated down in vacuo until the weight remained constant. In this way, 1.2 g of virtually pure stereoisomer (a), having the highest $R_f$ value, were obtained. In addition, 8.2 g of a mixture of the stereoisomers (b), (c)≧(a), (d) were obtained. Finally, 2.6 g were eluted, which were found by thin layer chromatography to contain a high concentration of the stereoisomer (d) (lowest $R_f$ value). This product was subjected to a second chromatography by the same procedure, over a silica S/hexane column (diameter 2 cm, height 22 cm). 1.2 g of a stereoisomer (d) which was shown to be virtually completely pure by thin layer chromatography was obtained.

$C_{20}H_{25}ClN_2O$ (344.89): calculated: C 69.65, H 7.31, Cl 10.28, N 8.12%; found: C 69.1, H 7.1, Cl 10.4, N 7.8% (Compound 107a); found: C 68.0, H 7.0, Cl 10.1, N 8.0% (Compound 107d); found: C 68.0, H 7.2, Cl 10.9, N 7.6% (Stereoisomer mixture 107b and 107c≧107a and 107d).

EXAMPLE 108 (COMPOUND 108)

3-Chlorophenyl-1-imidazolyl-(2-hydroxy-1-methoxymethyl-5-norbornen-2-yl)-methane 3.85 g (20 mmol) of N-(3-chlorobenzyl)-imidazole were dissolved in 45 ml of absolute THF and metallized with 13.4 ml (20 mmol) of 1.5M n-butyllithium/hexane solution at −70° C. After 30 minutes, a solution of 30.05 g (20 mmol) of 1-methoxymethylmethyl-5-norbornen-2-one in 20 ml of absolute THF was added, likewise at −70° C., and the mixture was stirred for a further 20 minutes at −70° C. and allowed to warm up to room temperature in the course of 2 hours. Thereafter, water was added and the mixture was extracted with ether. The residue (7.6 g) from the ether extract was crystallized from ethyl acetate/diisopropyl ether. After the crystalline substance had been filtered off under suction and dried, 3.75 g (=54.5% yield) of pure 3-chlorophenyl-1-imidazolyl-(2-hydroxy-1-methoxymethyl-5-norbornen-2-yl)-methane of melting point 161° C. were obtained.

$C_{19}H_{21}ClN_2O_2$ (344.85): calculated: C 66.18, H 6.14, Cl 10.28, N 8.12%; found: C 66.4, H 6.2, Cl 10.4, N 8.3%.

EXAMPLE 109 (COMPOUND 109)

1-(1-Imidazolyl)-1-(3-tolyl)-3,3-dimethylbutan-2-ol 39 ml (60 mmol) of a 1.55 molar n-butyllithium/hexane solution were added dropwise to a solution of 5.17 g (30 mmol) of N-(3-methylbenzyl)-imidazole and 3.49 g (30 mmol) of TMEDA in 60 ml of absolute THF at −70° C. The mixture was stirred for 30 minutes at about −70° C., after which a solution of 3.80 g (33 mmol) of 75% strength pivalaldehyde in 30 ml of absolute THF was added dropwise at about −70° C. in the course of 20 minutes, stirring was continued for 20 minutes at about −70° C. and the mixture was allowed to warm up to room temperature in the course of 2 hours. Thereafter, water was added, while cooling, and the resulting mixture was extracted with ether. The residue (9.3 g) from the ether extract was crystallized from a diisopropyl ether/hexane mixture. This gave 2.2 g of crystals, which consisted of about 90% of a by-product, 1-(3-methylbenzyl)-2-(1-hydroxy-2,2-dimethylprop-1-yl)-imidazole. The residue from the mother liquor was recrystallized from a diisopropyl ether/acetonitrile solution, and the crystalline product isolated in this procedure was then recrystallized twice from acetonitrile. 0.64 g (=8.3% of theory) of pure 1-(1-imidazolyl)-1-(3-tolyl)-3,3-dimethylbutan-2-ol of melting point 126° C. was obtained in this manner.

$C_{16}H_{22}N_2O$ (258.37): calculated: C 74.38, H 8.58, N 10.84%; found: C 73.7, H 8.6, N 10.8%.

EXAMPLE 110 (COMPOUND 110)

2-(4-Benzyloxyphenyl)-2-(1-imidazolyl)-1,1-diphenylethanol 34 ml (53 mmol) of 1,55 molar n-butyllithium/hexane solution were added dropwise to a solution of 6.87 g (26 mmol) of N-(4-benzyloxybenzyl)-imidazole and 3.03 g (26 mmol) of TMEDA in 100 ml of absolute THF at about −70° C., the mixture was stirred for 20 minutes at −70° C., a solution of 4.74 g of benzophenone in 40 ml of absolute THF was then added dropwise at −70° C., stirring was continued for 30 minutes at about −70° C. and for 1.5 hours at −70° C. to room temperature, and 350 ml of water were added, while cooling. The mixture was extracted with $CH_2Cl_2$. The residue (12 g) from the $CH_2Cl_2$ extract was chromatographed over a silica gel S/$CH_2Cl_2$ column (diameter 2.1 cm, height 55 cm) as described in Example 102. Fractions which were shown by thin layer chromatography to have a high concentration of the desired substance were combined and recrystallized from ethyl acetate/diisopropyl ether. 1.09 g (=16.4% yield) of pure 2-(4-benzyloxyyphenyl)-2-(1-imidazolyl)-1,1-diphenylethanol of melting point 204° C. were obtained in this manner.

$C_{30}H_{26}N_2O_2$ (446.55): calculated: C 80.69, H 5.87, N 6.27%; found: C 79.9, H 5.9, N 5.9%.

EXAMPLE 111 (COMPOUND 111)

2-(3-Chlorophenyl)-2-(1-imidazolyl)-1-(3-methyl-adamant-1-ylmethyl)-ethanol

A solution of 4.05 g (20 mmol) of 2-(3-methyl-1-adamant-yl)-acetaldehyde (95% pure) in 40 ml of absolute THF was added, at about −60° C., to a solution of 20 mmol of lithium-N-(3-chlorobenzyl)-imidazole in THF/hexane, the said solution being prepared analogously to Example 105, and the mixture was stirred for 45 minutes at about −60° C. and for 1.75 hours at −60° C. to room temperature. After about 200 ml of water had been added, the mixture was extracted with ether. The residue (8.8 g) from the ether extract was crystallized from diisopropyl ether, and the product obtained was then recrystallized from acetonitrile. After isolation, 1.90 g (=24.7% of theory) of 2-(3-chlorophenyl)-2-(1-imidazolyl)-1-(3-methyladamant-1-ylmethyl)-ethanol of melting point 126° C. were obtained as a diastereomer which was pure according to thin layer chromatography. According to thin layer chromatography, the mother liquor contained further amounts of the same diastereomer, and the other diastereomer as the principal component.

$C_{23}H_{29}ClN_2O$ (384.96): calculated: C 71.76, H 7.59, Cl 9.21, N 7.28%; found: C 71.8, H 7.4, Cl 9.5, N 7.3%.

EXAMPLE 112 (COMPOUND 112)

2-(3-Chlorophenyl)-2-(1-imidazolyl)-1-cyclopropyl-1-phenylethanol

A solution of 3.77 g of cyclopropyl phenyl ketone (97% pure) in 37 ml of absolute THF was added, at about −70° C., to a solution of 25 mmol of lithium-N-(3-chlorobenzyl)-imidazole in THF/hexane, the said solution being prepared analogously to Example 105, and the mixture was stirred for 20 minutes at about −70° C. and for 1.75 hours at −70° C. to room temperature. After about 200 ml of water had been added, the mixture was extracted with ether. The residue (6.1 g) from the ether extract was chromatographed over a silica gel S/$CH_2Cl_2$ column (diameter 2 cm, height 32 cm), with elution with $CH_2Cl_2$ and $CH_2Cl_2$/$C_2H_5OH$ mixtures having an increasing $C_2H_5OH$ content (up to a maximum of 1% by volume). Fractions which had similar compositions according to thin layer chromatography were combined. The diastereomer (A) (2.56 g) which was eluted first was found to be present in insufficient concentration and was therefore chromatographed again (see below). Thereafter, mixtures of the two diastereomers (A) and (B) were eluted, from which the diastereomer (B) (having the lower $R_f$ in thin layer chromatography) was crystallized using diisopropyl ether. After isolation and drying, 0.83 g (=9.8% of theory) of 2-(2-chlorophenyl)-2-(1-imidazolyl)-1-cyclopropyl-1-phenylethanol was obtained in the form of the pure diastereomer (B) (thin layer chromatography, lower $R_f$) of melting point 146° C. The mother liquor contained 0.90 g of a mixture of the diastereomers (A) and (B).

The diastereomer (A) (thin layer chromatography, higher $R_f$) (2.56 g) concentrated by chromatography was again chromatographed over a silica gel S/$CH_2Cl_2$ column (diameter 2 cm, height 30 cm), as described above. This procedure gave 2.04 g of highly concentrated diastereomer (A), which was obtained in crystalline form from ether/diisopropyl ether solution. After isolation and drying, 1.60 g (=18.9% of theory) of 2-(3-chlorophenyl)-2-(1-imidazolyl)-1-cyclopropyl-1-phenylethanol were obtained in the form of the pure diastereomer (B) (thin layer chromatography, higher $R_f$) of melting point 140° C. were obtained. The mother liquor contained 0.70 g of a mixture of the two diastereomers ((A)>(B)).

$C_{20}H_{19}ClN_2O$ (338.85): calculated: C 70.89, H 5.65, N 8.27%; found: C 71.1, H 5.8, N 8.1% (Diastereomer (A)); found: C 70.6, H 5.4, N 8.2% (Diastereomer (B)).

The following compounds of the formula I, in which Z=CH and $R^1$ and $R^2$=H, were obtained analogously to Examples 1 to 10 and 100 to 112:
TABLE 2
| Example No. | Aryl | Q | $R^3$ | $R^4$ | M.p. [°C.] |
|---|---|---|---|---|---|
| 113 |  | H | 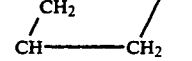 | | 249 |
| 114 |  | H | " | | 285 |
| 115 | 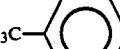 | H | " | | 270 |
| 116 | 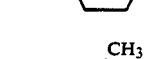 | H | " | | 258 |
| 117 | 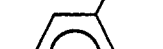 | H | " | | 286 |
| 118 |  | H | " | | 279 |
| 119 | 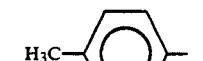 | H | " | | 273 |
| 120 | 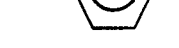 | H | " | | 169 |
| 121 |  | H |  | | 260 |
| 122 |  | H | " | | 256 |

TABLE 2-continued

| Example No. | Aryl | Q | R³ | R⁴ | M.p. [°C.] |
|---|---|---|---|---|---|
| 123 | phenoxyphenyl | H | " | | 206 |
| 124 | benzyloxyphenyl | H | " | | 104 |
| 125 | naphthalen-1-yl | H | " | | 206 |
| 126 | naphthalen-2-yl | H | " | | 230 |
| 127 | 1-bromonaphthalen-2-yl | H | " | | 273 |
| 128 | naphthalen-2-yl | H | as in 129 | H | amorphous |
| 129 | 3-chlorophenyl | H | adamantyl | H | 92 |
| 130 | 2-methylphenyl | H | adamantyl (C) | H | 219 |
| 131 | 3,4-dichlorophenyl | H | " | H | 187 |
| 132 | 4-chlorophenyl | H | phenyl | phenyl | 232 |

TABLE 2-continued

| Example No. | Aryl | Q | R³ | R⁴ | M.p. [°C.] |
|---|---|---|---|---|---|
| 133 | 3-Cl-C₆H₄- | H | " | " | 167 |
| 134 | 3-F-C₆H₄- | H | " | " | 192 |
| 135 | 2,4-Cl₂-C₆H₃- | H | " | " | 208 |
| 136 | 4-(C₆H₅CH₂O)-C₆H₄- | H | " | " | 204 |
| 137 | 2,4-Cl₂-C₆H₃- | H | 4-Cl-C₆H₄- | 4-Cl-C₆H₄- | 238 |
| 138 | 3-Cl-C₆H₄- | H | -C₆H₄-CH₂-CH₂-C₆H₄- | | 201 |
| 139 | 3-OCH₃-C₆H₄- | H | -C₆H₄-C₆H₄- (biphenyl-2,2'-diyl) | | 242 |
| 140 | 3-Cl-C₆H₄- | H | 9,10-dihydro-9,10-ethanoanthracene-11,12-diyl | H | 257 |
| 141 | 3-OCH₃-C₆H₄- | H | cyclohex-2-ene-1,2-diylbis(methylene) | H | oil |
| 142 | 3-Cl-C₆H₄- | H | " | H | oil |

TABLE 2-continued

| Example No. | Aryl | Q | R³ | R⁴ | M.p. [°C.] |
|---|---|---|---|---|---|
| 143 | 3-CH₃-C₆H₄ | H | -CH₂-C(CH₂OCH₃)(CH₂-CH=CH-CH₂-) (cyclopentenyl with CH₂OCH₃) | | 157 |
| 144 | 2,4-di-Cl-C₆H₃ | H | 1,2-(-CH₂-)₂-C₆H₄ | | 186 |
| 145 | 4-Cl-C₆H₄ | H | 4-Cl-C₆H₄ | H | 176 |
| 146 | 4-Cl-C₆H₄ | H | 2,4-di-Cl-C₆H₃ | H | 164 |
| 147 | 4-Cl-C₆H₄ | H | 4-OCH₃-C₆H₄ | H | 148 |
| 148 | 4-Cl-C₆H₄ | H | 2-Cl-C₆H₄ | H | oil |
| 149 | 2,4-di-Cl-C₆H₃ | H | 4-Cl-C₆H₄ | H | 224 |
| 150 | 2,4-di-Cl-C₆H₃ | H | 2,4-di-Cl-C₆H₃ | H | 227 |
| 151 | 3-Cl-C₆H₄ | H | 2,4,6-tri-CH₃-C₆H₂ | H (A)* (B) | 230 148 |
| 152 | 3-CH₃-C₆H₄ | H | 2-OCH₃-C₆H₄ | H | 123 |
| 153 | 3-Cl-C₆H₄ | H | 2,6-di-Cl-C₆H₃ | H (A)* (B) | 234 181 |

TABLE 2-continued

| Example No. | Aryl | Q | R³ | R⁴ | M.p. [°C.] |
|---|---|---|---|---|---|
| 154 | 3-Cl-phenyl | H | naphthalen-1-yl | H | 204 |
| 155 | 3-F-phenyl | H | C(CH₃)₃ | H | 137 |
| 156 | 3-Cl-phenyl | H | C(CH₃)₃ | CH₃ | 87 |
| 157 | 3,4-diCl-phenyl | H | C(CH₃)₃ | H | 133 |
| 158 | naphthalen-2-yl | H | C(CH₃)₃ | H | 156 |
| 159 | 3-Cl-phenyl | H | 2,6-bis(S—C(CH₃)₃)-phenyl | H (A,B)* | 140 |
| 160 | 3-Cl-phenyl | 2-CH₃ | adamantyl | | 294 |
| 161 | 3-Cl-phenyl | 2-C₂H₅ | " | | 258 |
| 162 | 3-Cl-phenyl | 2-CH₃ | C(CH₃)₃ | H | 227 |
| 163 | 3-Cl-phenyl | 2-C₂H₅ | C(CH₃)₃ | H | 209 |

TABLE 2-continued

| Example No. | Aryl | Q | R³ | R⁴ | M.p. [°C.] |
|---|---|---|---|---|---|
| 164 | Cl-phenyl | 2-C₂H₅ | 3,4-dimethylphenyl (CH₃, CH₃) | H (A)*) (B) | 119 186 |

The following compound of the formula I, in which Z = N and R¹ and R² = H, were obtained analogously to Examples 9 and 10:

| | | | | | |
|---|---|---|---|---|---|
| 165 | Cl-phenyl | H | noradamantyl (bicyclic CH/CH₂ structure) | | 131 |
| 166 | 3,4-(H₃CO)₂-phenyl | H | " | | 190 |
| 167 | 3-Cl-4-H₃C-phenyl | H | 4-Cl-phenyl + phenyl | | oil |

*)Diastereomers; R_f(A) > R_f(B) TLC, CH₂Cl₂/C₂H₅OH 10:1, silica gel 60 F 254, (Merck)

EXAMPLE 168

Resolution of racemate of (3-chlorophenyl)-(2-hydroxy-2-adamantyl)-(1-imidazolyl)-methane, compound according to Example 25 a) 43.0 g (125.4 mmol) of (3-chlorophenyl)-(2-hydroxy-2-adamantyl)-(1-imidazolyl)-methane and 18.83 g (125.4 mmol) of D(—)-tartaric acid were dissolved in a mixture of 67 ml of methanol and 440 ml of acetonitrile at the boiling point. When the solution was slowly cooled to room temperature, crystallization occurred. After 2 days, the crystals were filtered off under suction and washed with acetonitrile and ether and dried for 3 hours at 98° C./3-6 mbar. 23.50 g of (3-chlorophenyl)-(2-hydroxy-2-adamant-yl)-(1-imidazolyl)-methane hydrogen tartrate ([α]$_D$: (+) 4.26° (c=1.0, CH₃OH)) were obtained. This product was dissolved in a boiling mixture of 33 ml of methanol and 193 ml of acetonitrile and allowed to crystallize out at room temperature. After isolation as described above, 18.00 g of product [α]$_D^{22}$: (+) 5.30° (c=1.0, CH₃OH)) were obtained. These 18.00 g were recrystallized in an analogous manner from 26 ml of methanol and 151 ml of acetonitrile. 14.2 g of product [α]$_D^{22}$: (+) 5.53° (c=1.0, CH₃OH)) were obtained. A further recrystallization from 20 ml of methanol and 116 ml of acetonitrile gave 11.7 g of product ([α]$_D^{22}$: (+) 5.90° (c=1.0, CH₃OH)). Further recrystallization of this substance from 16 ml of methanol and 95 ml of acetonitrile in 9.60 g of (3-chlorophenyl)-(2-hydroxy-2-adamantyl)-(1-imidazolyl)-methane hydrogen tartrate ([α]$_D^{22}$: (+) 6.18° (c=1.0, CH₃OH)) as a pure diastereomeric salt of melting point 112°-113° C. (decomposition).

The mother liquors from the 3rd, 4th and 5th recrystallizations were combined and evaporated down in vacuo, and the remaining residue (8.20 g) was recrystallized from 11.5 ml of methanol and 66.5 ml of acetonitrile in a manner analogous to that described above. 5.4 g of product ([α]$_D^{22}$: (+) 5.81° (c=1.0, CH₃OH)) were obtained, and this product was recrystallized twice more from appropriate methanol/acetonitrile mixtures in an analogous manner. Thereafter, a further 3.60 g of pure diastereomeric hydrogen tartrate ([α]$_D^{22}$: (+) 6.20° (c=1.0, CH₃OH)) were obtained at this point. A total of 13.20 g (=42.7% of theory) of pure (+)-(3-chlorophenyl)-(2-hydroxy-2-adamantyl)-(1-imidazolyl)-methane hydrogen tartrate were obtained in this manner (starting from D(—)-tartaric acid).

C₂₄H₂₉ClN₂O₇ (492.97): calculated: C 58.48, H 5.93, Cl 7.19, N 5.68, O 22.72%; found: C 57.6, H 5.7, Cl 7.2, N 6.0, O 22.4%.

b) After about 43% of the (+)-enantiomer had been separated off, according to a), in the form of the pure diastereomeric (+)-hydrogen tartrate, the mother liquors were combined and evaporated down in vacuo. The remaining residue (47.5 g) was dissolved in a mixture of 450 ml of water and 300 ml of CH₂Cl₂, NaOH was added until the pH reached 9.5, the mixture was mixed thoroughly and the phases were then separated and the CH₂Cl₂ phase was dried and filtered and then evaporated down in vacuo. The residue was boiled up for a short time with about 230 ml of hexane, while stirring, and allowed to cool, and the crystalline substance, in which the (—)-enantiomer was present in excess, was filtered off under suction. 30 g of (3-chlorophenyl)-(2-hydroxy-2-adamantyl)-(1-imidazolyl)-methane ([α]$_D^{22}$: (—) 8.6° (c=1.05, CH₃OH)) (about 70% of theory) were obtained. These 30 g of product (87.5 mmol) and 13.13 g (87.5 mmol) of L(+)-tartaric acid were dissolved in a boiling mixture of 44 ml of methanol and 308 ml of acetonitrile and left to crystallize out while slowly cooling to room temperature. Further working up was carried out in a manner analogous to that described under a). The crystals isolated were then recrystallized four times from appropriate methanol/acetonitrile mixtures, after which 14.2 g ($\hat{=}45.9\%$ of theory) of quasi-pure (−)-(3-chlorophenyl)-(2-hydroxy-2-adamant-yl)-(1-imidazolyl)-methane hydrogen tartrate were obtained (starting from L(+)-tartaric acid) ($[\alpha]_D^{22}$: (−) 6.08° (c=1.0, $CH_3OH$)); m.p. 112°–113° C. (decomposition).

$C_{24}H_{29}ClN_2O_7$ (492.97): calculated: C 58.48, H 5.93, Cl 7.19, N 5.68, O 22.72%; found: C 57.2, H 5.6, Cl 6.9, N 6.1, O 21.3%.

c) A mixture of 9.86 g (20 mmol) of (+)-(3-chlorophenyl)-(2-hydroxy-2-adamantyl)-(1-imidazolyl)-methane hydrogen tartrate, 400 ml of $CH_2Cl_2$, 22 ml of 2N sodium hydroxide solution and 100 ml of water was shaken at room temperature until two clear phases were formed. After separation of the phases, the aqueous phase was extracted twice with $CH_2Cl_2$. The combined $CH_2Cl_2$ phases were dried, filtered and evaporated down in vacuo. The crystalline residue (6.86 g) was recrystallized from a mixture of 86 ml of acetonitrile and 60 ml of methanol. After isolation and drying of the crystalline substance, 5.34 g (=78% of theory) of pure (+)-(3-chlorophenyl)-(2-hydroxy-2-adamantyl)-(1-imidazolyl)-methane ($[\alpha]_D^{22}$: (+) 19.61° (c=1.05, $CH_3OH$)) of melting point 194.5° C. were obtained. A further amount (1.26 g, =18.4% of theory) of this substance ($[\alpha]_D^{22}$: (+) 19.09° (c=1.0, $CH_3OH$)) of melting point 193.5°–194.5° C. was obtained in an analogous manner from a residue from the mother liquor.

$C_{20}H_{23}ClN_2O$ (342.88): calculated: C 70.06, H 6.76, Cl 10.34, N 8.17%; found: C 70.0, H 6.7, Cl 10.5, N 8.2%.

PHARMACOLOGICAL TESTS

1. Test of the effect on tetrabenazine ptosis (TBZ)

Method

Test on mice (NMRI), male, weight 19–21 g, or on rats (Wistar), male, about 120 g body weight. Preparation administered orally, homogenized in 1% strength tylose, 1 hour before tetrabenzine, 40 mg/kg, administered subcutaneously (N=6/dose). During the test, 6 animals are present together in one container. To test for upper lid ptosis, the animals are placed individually on the table top. The extent of the ptosis (0–4 points) is assessed and is expressed as a percentage of the maximum score achievable. Evaluation is carried out 30 minutes after administration of tetrabenazine. Controls which have received only tetrabenazine are used for comparison. The dose which produces a 50% reduction (linear regression analysis) in the degree of ptosis in control animals treated only with the vehicle is determined as the $ED_{50}$.

2. Potentiation of the yohimbine toxicity in mice

Method

The toxicity of yohimbine, a blocker of presynaptic alpha-receptors, is potentiated by antidepressants (literature: R. M. Quinton, Brit. J. Pharmac. 21, 55–56 (1963)).

Male mice, NMRI strain, 20–22 g, were arranged in test groups of n=10. The test preparation was suspended in 1% strength aqueous Tylose ® slime and administered orally in a volume of 10 ml/kg. Control received only the vehicle.

After a pretreatment time of 1 hour, all animals received a dose of yohimbine hydrochloride, which dose, when administered alone, is non-toxic (20 mg/kg, administered subcutaneously). The dead animals were determined 18 hours after this treatment. (Calculation of the $LD_{50}$ by probit analysis).

3. Test of the promotion of stereotypes in rats

The tests were carried out on 130–140 g male Wistar rats. The stereotypes were assessed at 15 minute intervals during the first two hours after administration of the substance, and then at half-hourly intervals up to the 6th hour. The scale below was used.

| Symptoms | Number of points |
|---|---|
| Behavior as for control group | 0 |
| Increased sniffing | 1 |
| Sniffing and sitting up | 2 |
| Increased running, isolated shaking of the head and front paws | 3 |
| Occasional licking, biting and chewing | 4 |
| as for 4, but continuous | 5 |

The number of points were calculated as a total number per 6 hours, divided by the number of observations.

The $ED_{50}$ dose is the dose at which half the maximum possible number of points (5 points multiplied by the number of observations) is reached.

4. Inhibition of reabsorption of noradrenaline in synaptosomes

Method

Synaptosomes from rat brain are isolated by the method due to Whittaker (Handbook of Neurochemistry 2, 327–364, Editor A. Lajtha; London and New York, 1969), and the absorption of monoamine is measured by the method due to Schacht and Heptner (Biochemical Pharmac. 23, 3413–3422). The absorption of $^{14}C$ noradrenaline was measured in a Krebs-Henseleit bicarbonate buffer of pH 7.4, which contained 11 millimoles of glucose. 2.5 ml of the synaptosome suspension were incubated with labeled noradrenaline at 37° C. in the presence or absence of test substance. The incubation time was 4 minutes. Further absorption was then stopped by cooling with ice. In order to exclude non-specific adsorption, control samples were were incubated at 0° C. under otherwise identical conditions.

The absorbed amounts of noradrenaline were measured with the aid of membrane filtration technique, using a Millipore sampling manifold with cellulose nitrate filters of 25 mm diameter and 0.6 micrometer pore size. The synaptosomes were collected under reduced pressure, and the radioactivity was determined in a Packard Tricarb scintillation counter. The amount of noradrenaline collected was stated as the percentage of radioactivity added to the incubation mixture.

The $IC_{50}$ values (inhibition concentration) in the table below gives the concentrations of test substances which inhibit the absorption of $^{14}C$ noradrenaline by 50%.

| Results with the compound nomifensin as a comparative substance | | |
|---|---|---|
| | | Nomifensin |
| | Compound according to Example 25 | |
| Method 1, mouse | $ED_{50}$ = 0.79 mg/kg p.o. | $ED_{50}$ = 0.72 mg/kg p.o. |
| Method 1, rat | $ED_{50}$ = 10 mg/kg p.o. | $ED_{50}$ = 2.7 mg/kg p.o. |
| Method 2, mouse | $LD_{50}$ = 4.4 mg/kg p.o. | $LD_{50}$ = 8.6 mg/kg |
| Method 3, rat | no stereotypes up to 300 mg/kg p.o. | $ED_{50}$ = 11.9 mg/kg |
| Method 4 | $IC_{50}$ = $4.10^{-8}$M | $ID_{50}$ = $3.10^{-8}$M |
| | Compound according to Example 168a | |
| Method 1, mouse | $ED_{50}$ = 2.5 mg/kg p.o. | |
| Method 2, mouse | $LD_{50}$ = 4.6 mg/kg p.o. | |
| Method 3, rat | $ED_{50}$ = 30 mg/kg p.o. | |
| Method 4 | $IC_{50}$ = 1.2 $10^{-7}M$ | |
| Method 1, rat | $ED_{50}$ 5.5 mg/kg p.o. | |
| | Compound according to Example 106 | |
| Method 1, mouse | $ED_{50}$ = 1.5 mg/kg p.o. | |
| Method 2, mouse | $LD_{50}$ = 7 mg/kg p.o. | |
| Method 3, rat | $ED_{50}$ >>30 mg/kg p.o. | |
| Method 4 | $IC_{50}$ = $1.2 \times 10^{-7}$M | |
| | Compound according to Example 120 | |
| Method 1, mouse | $ED_{50}$ = 3 mg/kg p.o. | |
| Method 2, mouse | $ED_{50}$ = 3 mg/kg p.o. | |
| | Compound according to Example 126 | |
| Method 1, mouse | $ED_{50}$ = 3 mg/kg p.o. | |
| Method 2, mouse | $LD_{50}$ = 3.2 mg/kg p.o. | |
| | Compound according to Example 105 | |
| Method 1, mouse | $ED_{50}$ = 3.7 mg/kg p.o. | |
| Method 2, mouse | $LD_{50}$ = 8.5 mg/kg p.o. | |
| Method 3, rat | $ED_{50}$ >>30 mg/kg p.o. | |
| | Compound according to Example 4 | |
| Method 1, mouse | $ED_{50}$ = 3.0 mg/kg p.o. | |
| Method 2, mouse | $LD_{50}$ = 5.3 mg/kg p.o. | |
| Method 3, rat | $Ed_{50}$ >>30 mg/kg p.o. | |

We claim:
1. A compound of the formula I

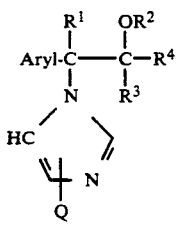

in which
aryl is a radical

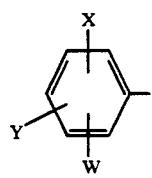

or a 1- or 2-naphthyl radical which is unsubstituted or substituted by U and/or a substituent V, where
X is H, $(C_1-C_4)$-alkyl, phenyl, fluorine, chlorine, bromine, $(C_1-C_4)$-alkoxy,

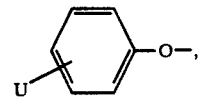

$(C_1-C_4)$-alkylthio, $-NR_2^5$, in which the radicals $R^5$ which are identical or different are $(C_1-C_4)$-alkyl or together with the nitrogen atom are a pyrrolidine, piperidine or morpholine radical, or X is $CF_3$ or a benzyloxy group which is unsubstituted or carries one or two substituents in the phenyl radical, the substituents which are identical or different are fluorine, chlorine, $OCH_3$, $OC_2H_5$ or $(C_1-C_3)$-alkyl, Y is H, $(C_1-C_4)$-alkyl, fluorine, chlorine, bromine, $(C_1-C_4)$-alkoxy or $(C_1-C_4)$-alkylthio, or X and Y together in the 2,3- or 3,4-position are a $-(CH_2)_L-$chain, in which L=3 or 4, $-OCH_2CH_2-$ or $-O-CH_2-O$, W is H, $CH_3$ or $OCH_3$, V is $(C_1-C_4)$-alkyl, phenyl, fluorine, chlorine, bromine, hydroxyl, $(C_1-C_4)$-alkoxy, $(C_1-C_4)$-alkylthio, $-NR_2^5$, in which $R^5$ is $(C_1-C_4)$-alkyl or together with the nitrogen atom is a pyrrolidine, piperidine or morpholine radical, benzyloxy or $CF_3$, and U is $CH_3$, F, Cl or $OCH_3$, Q is H or $(C_1-C_4)$-alkyl,
$R^1$ is H
$R^2$ is H, $(C_1-C_4)$-alkyl, $(C_3-C_5)$-alkenyl or $(C_3-C_5)$-alkynyl,
$R^3$ is $(C_1-C_{12})$-alkyl, $(C_3-C_{10})$-alkenyl, $(C_3-C_{12})$-cycloalkyl, $(C_5-C_{12})$-cycloalkenyl, $(C_7-C_{12})$-polycycloalkyl, $(C_7-C_{12})$-polycycloalkenyl, $(C_5-C_{12})$-cycloalkyl-$(C_1-C_4)$-alkyl, $(C_5-C_{12})$-cycloalkylidene-$(C_2-C_4)$-alkyl, $(C_5-C_{12})$-cycloalkenyl-$(C_1-C_4)$-alkyl, $(C_7-C_{12})$-polycycloalkyl-$(C_2-C_4)$-alkyl, $(C_7-C_{12})$-polycycloalkylidene-$(C_1-C_4)$-alkyl, $(C_7-C_{12})$-polycycloalkenyl-$(C_1-C_4)$-alkyl or these hydrocarbon radicals which are unsubstituted or carry up to 3 substituents, the substituents which are identical or different being F, Cl or Br and whereby the cyclic hydrocarbon radicals may additionally be substituted by $(C_1-C_4)$-alkyl, and $R^4$ is H $(C_1-C_{12})$-alkyl, $(C_3-C_{10})$-alkenyl, $(C_3-C_{12})$-cycloalkyl, $(C_5-C_{12})$-cycloalkenyl, $(C_7-C_{12})$-polycycloalkyl, $(C_7-C_{12})$-polycycloalkenyl, $(C_5-C_{12})$-cycloalkyl-$(C_1-C_4)$-alkyl, $(C_5-C_{12})$-cycloalkylidene-$(C_2-C_4)$-alkyl, $(C_5-C_{12})$-cycloalkenyl-$(C_1-C_4)$-alkyl, $(C_7-C_{12})$-polycycloalkyl-$(C_1-C_4)$-alkyl, $(C_7-C_{12})$-polycyclo-alkylidene-$(C_2-C_4)$-alkyl, $(C_7-C_{12})$-polycycloalkenyl-$(C_1-C_4)$-alkyl or these hydrocarbon radicals which are unsubstituted or carry up to 3 substituents, the substituents which are identical or different being F, Cl or Br and whereby the cyclic hydrocarbon radicals may additionally be substituted by $(C_1-C_4)$-alkyl, or $R^4$ is a phenyl-$(C_2-C_4)$-alkyl group which is unsubstituted or carries up to 3 substituents in the phenyl radical, the substituents which are identical or different being F, Cl, Br, $(C_1-C_4)$-alkoxy, $(C_1-C_4)$-alkyl or $(C_1-C_4)$-alkylthio, or $R^4$ is a naphthyl-$(C_1-C_4)$-alkyl group which is unsubstituted or carries up to 2 substituents in the naphthyl radical, the substituents which are identical or different being F, Cl, Br, $OCH_3$, $OC_2H_5$ or $(C_1-C_4)$-alkyl, and a physiologically tolerated acid addition salt thereof and its stereoisomers and optically active enantiomers.

2. A compound I as claimed in claim 1, wherein at least one of the following characteristics is fulfilled:
aryl is a radical

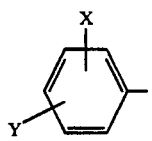

or a 2-naphthyl radical which is unsubstituted or substituted by a substituent V, in which
X is H, $(C_1-C_4)$-alkyl, phenyl, F, Cl, Br, $(C_1-C_4)$-alkoxy, 3-$CF_3$ or a benzyloxy group,
Y is H, $CH_3$, Cl or $OCH_3$ and
V is $(C_1-C_4)$-alkyl, Cl, Br, OH or $OCH_3$,
Q is H, $CH_3$ or $C_2H_5$,
$R^1$ is H,
$R^2$ is H,
$R^3$ is $(C_1-C_8)$-alkyl, $(C_3-C_{10})$-alkenyl, $(C_3-C_{12})$-cycloalkyl, $(C_5-C_{12})$-cycloalkenyl, $(C_7-C_{12})$-polycycloalkyl, $(C_7-C_{12})$-polycycloalkenyl, $(C_5-C_{12})$-cycloalkyl-$(C_1-C_4)$-alkyl, $(C_5-C_{12})$-cycloalkylidene-$(C_1-C_4)$-alkyl, $(C_5-C_{12})$-cycloalkenyl-$(C_2-C_4)$-alkyl, $(C_7-C_{12})$-polycycloalkyl-$(C_1-C_4)$-alkyl, $(C_7-C_{12})$-polycycloalkylidene-$(C_2-C_4)$-alkyl, $(C_7-C_{12})$-polycycloalkenyl-$(C_1-C_4)$-alkyl or these cyclic hydrocarbon radicals possessing up to 3 identical or different substituents, the latter being F, Cl, Br or $CH_3$, and
$R^4$ is H, $(C_1-C_{12})$-alkyl, $(C_3-C_5)$-alkenyl, cyclopropyl, $(C_5-C_8)$-cycloalkyl, or a phenyl-$(C_2-C_4)$-alkyl or naphthyl-$(C_1-C_4)$-alkyl group which is unsubstituted or carries up to 2 substituents in the phenyl radical or naphthyl radical, the substituents which are identical or different being F, Cl, Br, $OCH_3$, $OC_2H_5$ or $(C_1-C_4)$-alkyl.

3. A compound I as claimed in claim 1 or 2, wherein at least one of the following characteristics is fulfilled:
aryl is a radical

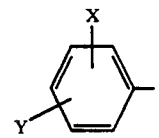

in which
X is $(C_1-C_4)$-alkyl, phenyl, F, Cl or $(C_1-C_4)$-alkoxy,
Y is H, $CH_3$, Cl or $OCH_3$ and the 6-position is always unsubstituted, or a 2-naphthyl radical which is unsubstituted or monosubstituted by Br or Cl,
Q, $R^1$ and $R^2$ are H,
$R^3$ is $(C_1-C_8)$-alkyl, $(C_5-C_7)$-cycloalkyl, $(C_7-C_{12})$-polycycloalkyl, $(C_7-C_{12})$-polycycloalkenyl, $(C_7-C_{12})$-polycycloalkyl-$(C_1-C_4)$-alkyl or these cyclic hydrocarbon radicals possessing one substituent or 1 or 2 identical or different substituents, the substituents being Cl, Br or $CH_3$, and
$R^4$ is H, $(C_1-C_4)$-alkyl, cyclopentyl, cyclohexyl or cyclopropyl.

4. A method for the treatment of a mammal in need of antimycotic action which comprises administering to said mammal a pharmaceutically effective amount of a compound of the formula I as claimed in claim 1 as an antimycotic.

5. A pharmaceutical composition having an antimycotic action which contains a pharmaceutically effective amount of a compound of the formula I as claimed in claim 1 together with a pharmaceutically suitable carrier.

6. A method for the treatment of a mammal in need of antidepressant action which comprises administering to said mammal a pharmaceutically effective amount of a compound of the formula I as claimed in claim 1 as an antidepressant.

7. A pharmaceutical composition having an antidepressant action, which contains an effective amount of a compound of the formula I as claimed in claim 1 together with a pharmaceutically suitable carrier.

* * * * *